(12) United States Patent
Denny et al.

(10) Patent No.: US 8,210,171 B2
(45) Date of Patent: Jul. 3, 2012

(54) TUBULAR DRY POWDER DRUG CONTAINMENT SYSTEMS, ASSOCIATED INHALERS AND METHODS

(75) Inventors: John Denny, Cary, NC (US); Michael King, Durham, NC (US); Patrick D. Lopath, Stamford, CT (US); Jeffrey Alan Warden, Raleigh, NC (US)

(73) Assignee: Oriel Therapeutics, Inc., Durham, NC (US)

( * ) Notice: Subject to any disclaimer, the term of this patent is extended or adjusted under 35 U.S.C. 154(b) by 1124 days.

(21) Appl. No.: 11/575,175

(22) PCT Filed: Sep. 12, 2005

(86) PCT No.: PCT/US2005/032371
§ 371 (c)(1),
(2), (4) Date: Feb. 11, 2008

(87) PCT Pub. No.: WO2006/031712
PCT Pub. Date: Mar. 23, 2006

(65) Prior Publication Data
US 2008/0168987 A1    Jul. 17, 2008

Related U.S. Application Data

(60) Provisional application No. 60/609,485, filed on Sep. 13, 2004.

(51) Int. Cl.
*A61M 15/00* (2006.01)
*B65D 83/06* (2006.01)

(52) U.S. Cl. .......... 128/203.15; 128/203.12; 128/203.23

(58) Field of Classification Search .......... 128/200.14–200.23, 200.24, 203.12, 128/203.15, 203.21, 203.23; 604/58; 222/4, 222/23–51, 519–525
See application file for complete search history.

(56) References Cited

U.S. PATENT DOCUMENTS

| | | | |
|---|---|---|---|
| 3,173,840 A | 3/1965 | Hostetler et al. | |
| 3,948,264 A | 4/1976 | Wilke et al. | |
| 3,980,074 A | 9/1976 | Watt et al. | |
| 3,991,761 A | 11/1976 | Cocozza et al. | |
| 4,040,536 A | 8/1977 | Schwarz | |
| 4,940,051 A * | 7/1990 | Lankinen | 128/200.18 |

(Continued)

FOREIGN PATENT DOCUMENTS

DE    19835346    2/2002

(Continued)

OTHER PUBLICATIONS

International Search Report and Written Opinion mailed Mar. 13, 2006 for corresponding PCT application No. PCT/US2005/032371 (24 pages).

(Continued)

*Primary Examiner* — Justine Yu
*Assistant Examiner* — Valerie L Skorupa
(74) *Attorney, Agent, or Firm* — Myers Bigel Sibley & Sajovec, P.A.

(57) ABSTRACT

Pharmaceutical dry powder containers adapted for use in an inhaler and associated inhalers and kits thereof include at least a pair of cooperating generally tubular members, including an inner member and a generally tubular outer member sized and configured to slidably receive the inner member. In operation, at least one of the inner or outer members slide relative to the other to release a pharmaceutical dry powder.

12 Claims, 20 Drawing Sheets

POSITIONING A DRUG CONTAINMENT SYSTEM COMPRISING COOPERATING FIRST AND SECOND GENERALLY TUBULAR MEMBERS DEFINING AT LEAST ONE SEALED DRUG COMPARTMENT HOLDING DRY POWDER INTO AN INHALER.
100

SLIDING THE FIRST AND/OR SECOND TUBULAR MEMBER IN A PREDETERMINED DIRECTION TO THEREBY OPEN THE SEALED DRUG COMPARTMENT AND EXPOSE THE DRY POWDER.
110

U.S. PATENT DOCUMENTS

| | | | |
|---|---|---|---|
| 4,991,605 A | 2/1991 | Keritsis | |
| 5,351,683 A * | 10/1994 | Chiesi et al. | 128/203.12 |
| 5,533,502 A | 7/1996 | Piper | |
| 5,562,918 A | 10/1996 | Stimpson | 424/451 |
| 5,641,510 A | 6/1997 | Clark et al. | |
| 5,655,523 A | 8/1997 | Hodson et al. | |
| 5,687,746 A | 11/1997 | Rose et al. | 131/273 |
| 5,727,607 A | 3/1998 | Ichikawa et al. | |
| 5,769,073 A | 6/1998 | Eason et al. | |
| 5,909,829 A | 6/1999 | Wegman et al. | |
| 5,947,169 A | 9/1999 | Wegman et al. | |
| 5,960,609 A | 10/1999 | Abrams et al. | |
| 6,014,969 A * | 1/2000 | Lloyd et al. | 128/200.14 |
| 6,026,809 A | 2/2000 | Abrams et al. | |
| 6,029,663 A | 2/2000 | Eisele et al. | |
| 6,196,219 B1 * | 3/2001 | Hess et al. | 128/200.21 |
| 6,428,809 B1 | 8/2002 | Abrams et al. | |
| 6,446,626 B1 * | 9/2002 | Virtanen | 128/200.14 |
| 6,578,571 B1 * | 6/2003 | Watt | 128/200.14 |
| 6,684,880 B2 * | 2/2004 | Trueba | 128/200.16 |
| 6,845,772 B2 * | 1/2005 | Braithwaite et al. | 128/203.15 |
| 6,889,690 B2 | 5/2005 | Crowder et al. | |
| 6,923,175 B2 | 8/2005 | Poole et al. | |
| 6,971,383 B2 | 12/2005 | Hickey et al. | |
| 6,985,798 B2 | 1/2006 | Crowder et al. | |
| 7,118,010 B2 | 10/2006 | Crowder et al. | |
| 7,305,986 B1 | 12/2007 | Steiner et al. | |
| 2002/0092521 A1 * | 7/2002 | Sullivan et al. | 128/200.24 |
| 2003/0075172 A1 * | 4/2003 | Johnson et al. | 128/200.24 |
| 2003/0097092 A1 * | 5/2003 | Flaherty | 604/67 |
| 2003/0209245 A1 * | 11/2003 | Poole et al. | 128/203.15 |
| 2004/0055598 A1 | 3/2004 | Crowder et al. | |
| 2004/0060557 A1 * | 4/2004 | Newton et al. | 128/203.15 |
| 2004/0255940 A1 | 12/2004 | Pera | |
| 2005/0022812 A1 * | 2/2005 | Hrkach | 128/203.15 |
| 2005/0172961 A1 | 8/2005 | Nesbitt | |

FOREIGN PATENT DOCUMENTS

| | | |
|---|---|---|
| WO | WO 91/13646 | 9/1991 |
| WO | WO 01/07107 | 2/2001 |
| WO | WO01/30430 | 5/2001 |
| WO | WO 01/68169 A1 | 9/2001 |
| WO | WO 03/080149 | 10/2003 |

OTHER PUBLICATIONS

Crowder et al. "2001: An Odyssey in Inhaler Formulation and Design" *Pharmaceutical Technology* 25(7):99-113 (2001).

Hickey et al. "A New Millennium for Inhaler Technology" *Pharmaceutical Technology* 21(6):7 pages (1997).

Peart et al. "New Developments in Dry Powder Inhaler Technology" *American Pharmaceutical Review* 4(3):37-45 (2001).

Prime et al. "Review of dry powder inhalers" *Advanced Drug Delivery Reviews* 26:51-58 (1997).

* cited by examiner

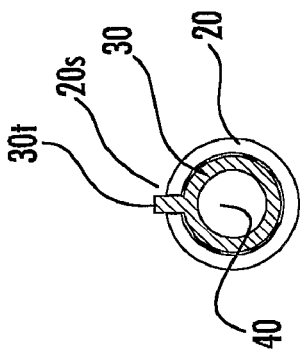
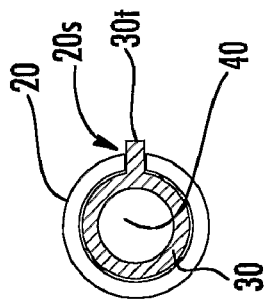
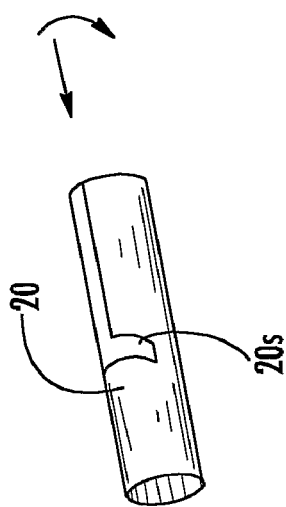

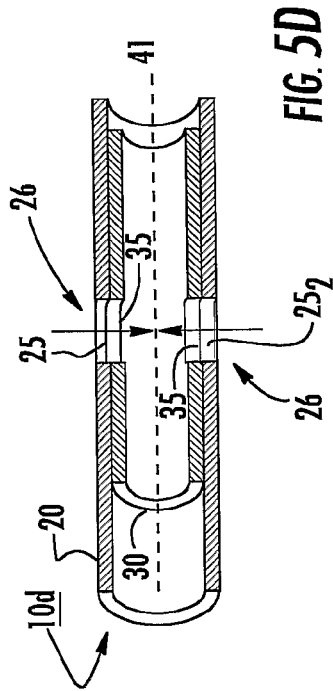
FIG. 5D
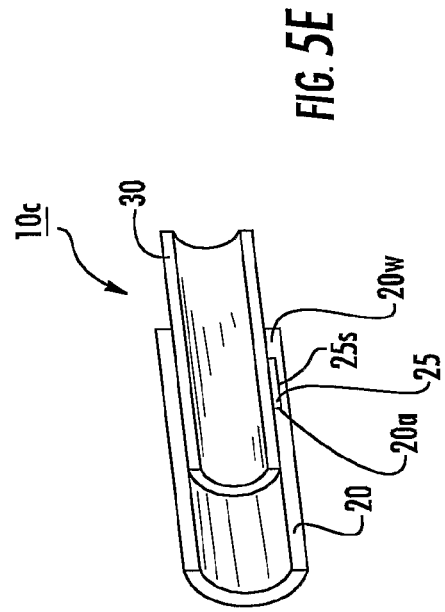
FIG. 5E
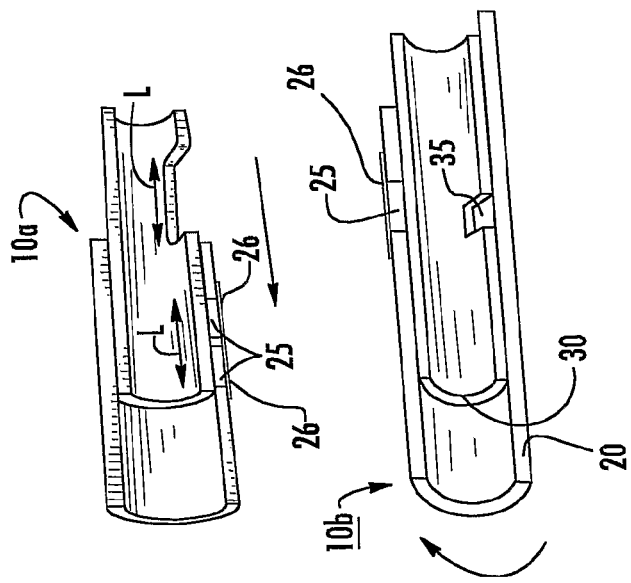
FIG. 5A
FIG. 5B
FIG. 5C

CLOSED POSITION

OPEN POSITION

←— AIRFLOW

OPEN POSITION

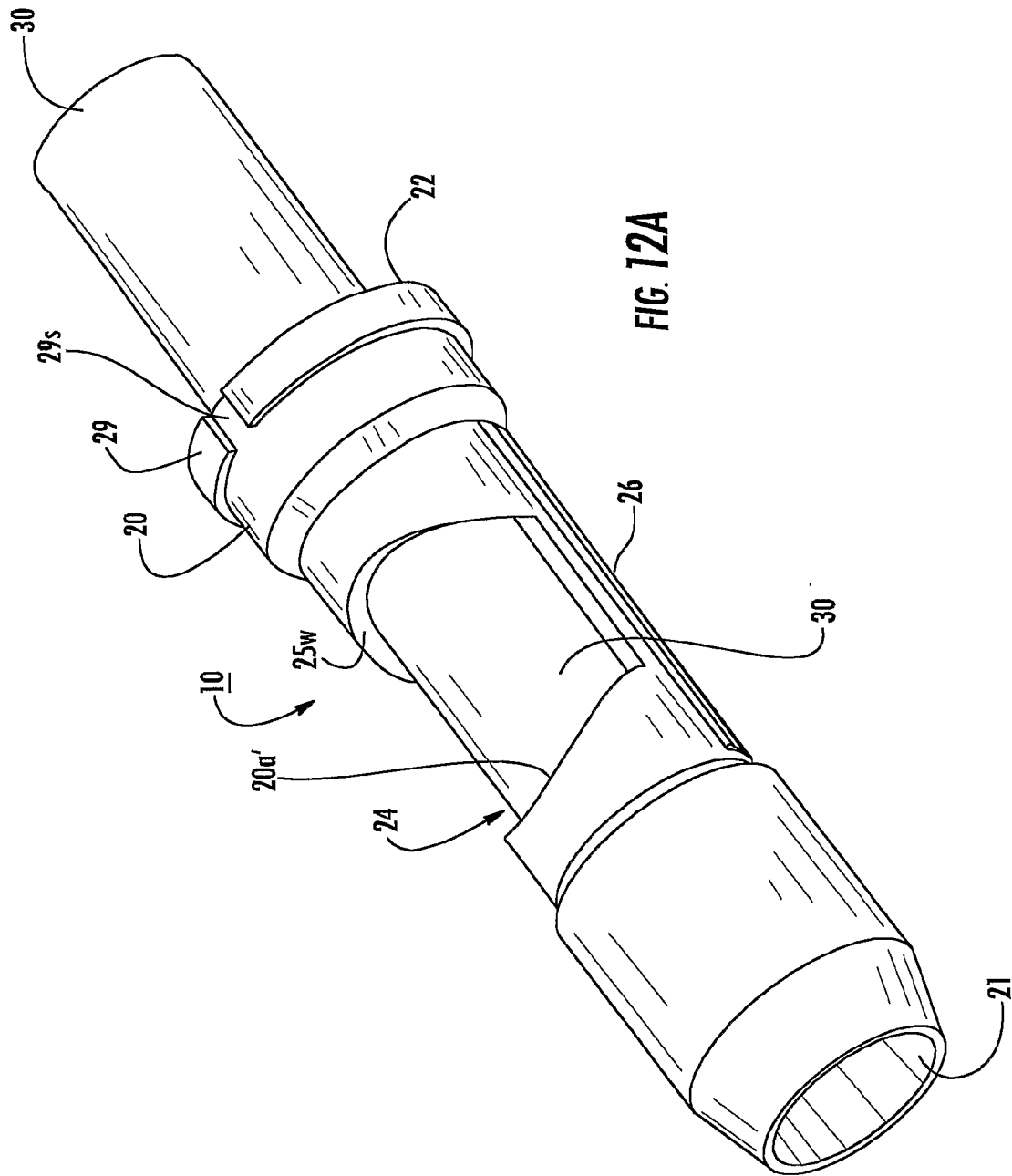

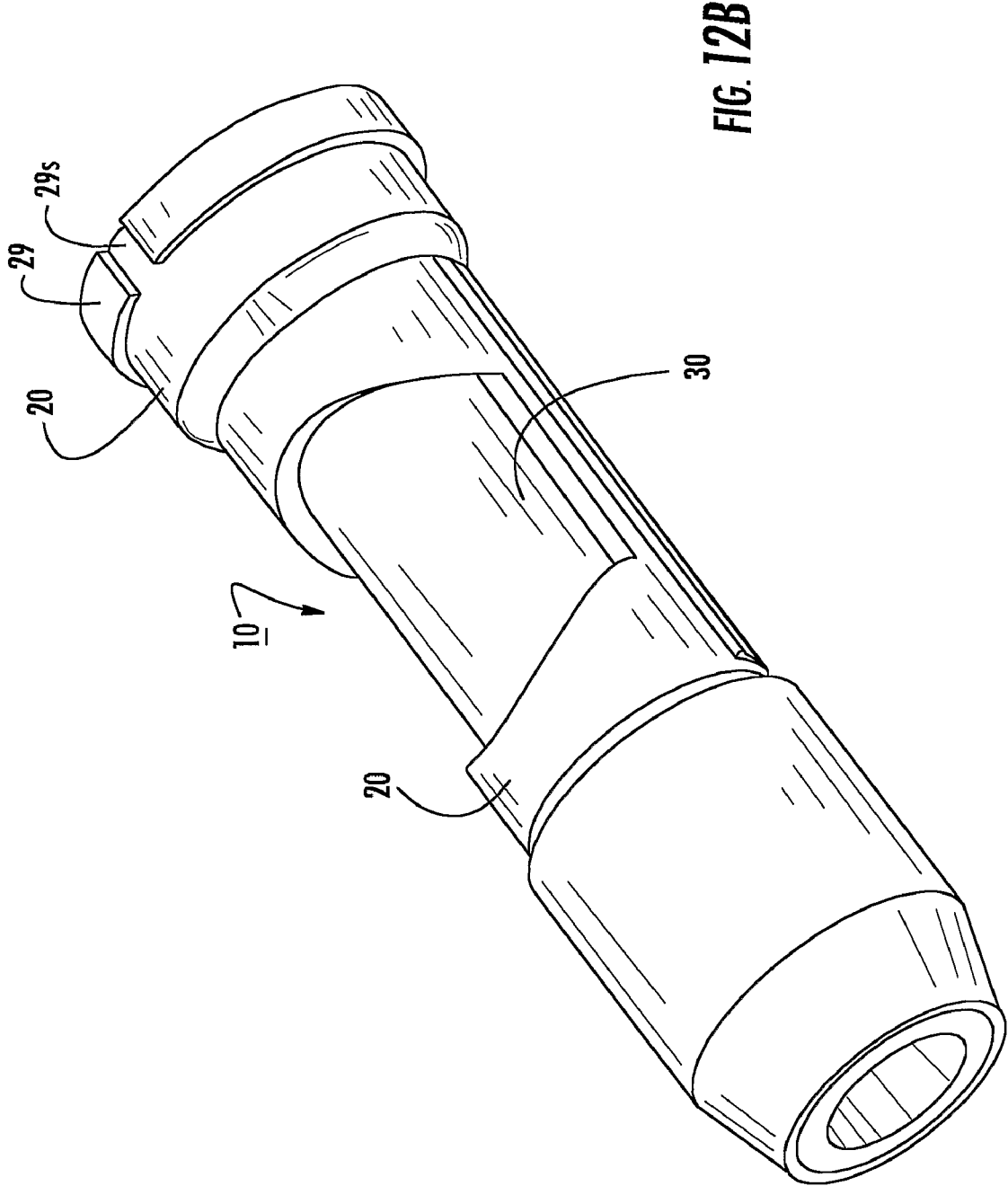

TUBULAR DRY POWDER DRUG CONTAINMENT SYSTEMS, ASSOCIATED INHALERS AND METHODS

RELATED APPLICATIONS

This application is a 35 USC 371 national phase application of PCT/US2005/032371, filed Sep. 12, 2005 which claims the benefit of priority to U.S. Provisional Patent Application Ser. No. 60/609,485 filed Sep. 13, 2004, the contents of which are hereby incorporated by reference as if recited in full herein.

FIELD OF THE INVENTION

The present invention relates to drug containment and/or dispensing systems suitable for dry powders formulated for delivery as inhalant aerosols.

BACKGROUND OF THE INVENTION

Dry powder inhalers (DPIs) represent a promising alternative to pressurized pMDI (pressurized meted dose inhaler) devices for delivering drug aerosols without using CFC propellants. See generally, Crowder et al., 2001: *an Odyssey in Inhaler Formulation and Design*, Pharmaceutical Technology, pp. 99-113, July 2001; and Peart et al., *New Developments in Dry Powder Inhaler Technology*, American Pharmaceutical Review, Vol. 4, n. 3, pp. 37-45 (2001). Typically, the DPIs are configured to deliver a powdered drug or drug mixture that includes an excipient and/or other ingredients.

Generally described, known single and multiple dose dry powder DPI devices use: (a) individual pre-measured doses in blisters containing the drug, which can be inserted into the device prior to dispensing; or (b) bulk powder reservoirs which are configured to administer successive quantities of the drug to the patient via a dispensing chamber which dispenses the proper dose. See generally Prime et al., *Review of Dry Powder Inhalers,* 26 Adv. Drug Delivery Rev., pp. 51-58 (1997); and Hickey et al., *A new millennium for inhaler technology,* 21 Pharm. Tech., n. 6, pp. 116-125 (1997).

In operation, DPI devices strive to administer a uniform aerosol dispersion amount in a desired physical form (such as a particulate size) of the dry powder into a patient's airway and direct it to a desired deposit site(s). If the patient is unable to provide sufficient respiratory effort, the extent of drug penetration, especially to the lower portion of the airway, may be impeded. This may result in premature deposit of the powder in the patient's mouth or throat.

A number of obstacles can undesirably impact the performance of the DPI. For example, the small size of the inhalable particles in the dry powder drug mixture can subject them to forces of agglomeration and/or cohesion (i.e., certain types of dry powders are susceptible to agglomeration, which is typically caused by particles of the drug adhering together), which can result in poor flow and non-uniform dispersion. In addition, as noted above, many dry powder formulations employ larger excipient particles to promote flow properties of the drug. However, separation of the drug from the excipient, as well as the presence of agglomeration, can require additional inspiratory effort, which, again, can impact the stable dispersion of the powder within the air stream of the patient. Unstable dispersions may inhibit the drug from reaching its preferred deposit/destination site and can prematurely deposit undue amounts of the drug elsewhere.

Further, some dry powder inhalers can retain a significant amount of the drug within the device, which can be especially problematic over time. In addition, the hygroscopic nature of many of these dry powder drugs may also require that the device be cleansed (and dried) at periodic intervals.

Some inhalation devices have attempted to resolve problems attendant with conventional passive inhalers. For example, U.S. Pat. No. 5,655,523 proposes a dry powder inhalation device which has a deagglomeration/aerosolization plunger rod or biased hammer and solenoid, and U.S. Pat. No. 3,948,264 proposes the use of a battery-powered solenoid buzzer to vibrate the capsule to effectuate the release of the powder contained therein. These devices propose to facilitate the release of the dry powder by the use of energy input independent of patient respiratory effort. U.S. Pat. No. 6,029,663 to Eisele et al. proposes a dry powder inhaler delivery system with a rotatable carrier disk having a blister shell sealed by a shear layer that uses an actuator that tears away the shear layer to release the powder drug contents. The device also proposes a hanging mouthpiece cover that is attached to a bottom portion of the inhaler. U.S. Pat. No. 5,533,502 to Piper proposes a powder inhaler using patient inspiratory efforts for generating a respirable aerosol and also includes a rotatable cartridge holding the depressed wells or blisters defining the medicament holding receptacles. A spring-loaded carriage compresses the blister against conduits with sharp edges that puncture the blister to release the medication that is then entrained in air drawn in from the air inlet conduit so that aerosolized medication is emitted from the aerosol outlet conduit. The contents of these patents are hereby incorporated by reference as if stated in full herein.

More recently, Hickey et al., in U.S. patent application Ser. No. 10/434,009 and PCT Patent Publication No. WO 01/68169A1 and related U.S. National Stage patent application Ser. No. 10/204,609, have proposed a DPI system to actively facilitate the dispersion and release of dry powder drug formulations during inhalation using piezoelectric polymer film elements which may promote or increase the quantity of fine particle fraction particles dispersed or emitted from the device over conventional DPI systems. The contents of these documents are hereby incorporated by reference as if recited in full herein.

Notwithstanding the above, there remains a need for alternative inhalers and/or blister packages that can be used with dry powder inhalers.

SUMMARY OF EMBODIMENTS OF THE INVENTION

In some embodiments, pharmaceutical dry powder containers adapted for use in an inhaler and associated inhalers and/or kits thereof include a generally tubular inner member and a generally tubular outer member sized and configured to slidably receive the inner member. In operation, at least one of the inner or outer members slide in a target primary direction to release a physiologically active agent, typically a pharmaceutical product such as, but not limited to, a pharmaceutical dry powder.

The containers can be configured to include a meted single or (unitized) portion of a single dose. In particular embodiments, the containers may include meted amounts and/or doses of dry powder disposed in a plurality of spaced apart drug compartments for in situ combination mixing/dosing. The doses may be of the same drug or different drugs.

In particular embodiments, the dry powder packages can have piezoelectric components. Alternatively or additionally, the inhaler can have an active and/or electrically excitable piezoelectric component forming a part of the flow path away from a respective drug compartment to facilitate fluidic drug dispersion.

Some embodiments are directed to kits of different unitized amounts of dry powder containers adapted for use in an inhaler. The kits can include a first set of generally tubular members and a second set of generally tubular members. Each of the first and second set can comprise a different predetermined meted (unitized) amount of dry powder drug held therein In particular embodiments, each generally tubular member of the first and second set are configured as snugly abutting inner and outer tube pairs that cooperate to seal and slide to release the respective dry powder held therein. The first and second set of generally tubular members can have generally rigid bodies and be single-use disposable.

Other embodiments are directed to inhalers that include a body having an inspiratory airflow path and an elongate chamber configured to receive a generally tubular drug containment system having at least one sealed drug compartment.

The generally tubular drug containment system can be held in the inhaler elongate chamber. The generally tubular drug containment system can include generally concentrically configured inner and outer generally tubular member pairs.

Additional embodiments are directed to methods of operating a dry powder inhaler. The methods include: (a) placing a drug containment system comprising slidably cooperating inner and outer generally tubular members and at least one sealed drug compartment holding dry powder into an inhaler; (b) sliding the inner (and/or outer) tubular member in a target primary direction to thereby open the sealed drug compartment.

In some embodiments, the methods may also include vibrating (the body and/or a ceiling or floor of) the drug compartment and/or tubular drug containment system to facilitate dispersion of the dry powder.

Additional embodiments are directed to methods of tracking and dispensing a variable bolus amount of inhalant drug from an inhaler. The methods include: (a) accepting user input to display a variable first unitized target bolus amount on the inhaler in situ; (b) identifying a second unitized sub-bolus amount associated with an amount of drug in a drug containment system in an active inhalant position in the inhaler; and (c) decrementing the first target bolus amount by the second sub-bolus amount to reveal the remaining unitized bolus amount needed to meet the target bolus amount.

In particular embodiments, the identifying and decrementing steps are repeated to administer the target bolus.

Still other embodiments are directed to methods of fabricating a dry powder medicament containment system. The methods include: (a) sliding a first generally tubular member comprising at least one aperture formed into a wall thereof into a second generally tubular member comprising at least one aperture formed into a wall thereof so that the first generally tubular member defines a sealed closed surface under the at least one aperture of the second generally tubular member; (b) placing dry powder into the at least one aperture of the second generally tubular member; then (c) attaching a sealant layer over the second generally tubular member at least one aperture to thereby define a sealed drug containment system with dry powder releaseably sealably captured therein.

In some embodiments, the placing step comprises meting a desired amount of dry powder drug into the aperture and the methods can also include: (d) sterilizing the first and second tubular members prior to the placing step; and (e) packaging the sealed drug containment system in a sterile package after the attaching step. The methods can further include placing an unitized identifier on the container so that a user can readily identify the unitized dose amount therein.

Other methods of fabricating a dry powder medicament containment system, include: (a) providing a first generally tubular member having at least one aperture formed into a wall thereof; (b) placing dry powder into the at least one aperture of the first generally tubular member; then (c) sliding the first generally tubular member into a second generally tubular member comprising at least one aperture formed into a wall thereof so that the second generally tubular member is misaligned with the first tubular member aperture to define a sealed closed surface over the at least one aperture of the first generally tubular member to thereby define a sealed drug containment system with dry powder releaseably sealably captured therein.

In some particular embodiments, the first and second generally tubular member at least one apertures extend through the respective walls. The method may include attaching a sealant layer over the first tubular member at least one aperture before the placing and sliding steps.

Still other methods are directed to fabricating a single-use disposable dry powder medicament containment system. The methods include: (a) providing a first generally tubular member comprising spaced at least one filling aperture and at least one drug compartment with a drug compartment aperture formed through a wall thereof; (b) introducing a meted amount of a dry powder drug through the at least one filling aperture into the at least one drug compartment; and (c) sliding a second generally tubular member into the first tubular member to provide a closed surface over the drug compartment aperture to thereby define a sealed drug compartment.

In some embodiments, the method may also include attaching a sealant layer over an outer surface of the first generally tubular member to span the at least one aperture before the introducing step.

It is noted that aspects of the invention may be embodied as hardware, software or combinations of same, i.e., devices and/or computer program products. These and other objects and/or aspects of the present invention are explained in detail in the specification set forth below.

BRIEF DESCRIPTION OF THE DRAWINGS

FIG. 1 is a flow chart of operations that can be used to provide an inhalant medicament from a sealed drug containment system according to embodiments of the present invention.

FIG. 2 is a flow chart of operations that can be used to unseal a drug containment system according to embodiments of the present invention.

FIG. 3A is a side perspective view of a tubular drug containment system according to embodiments of the present invention.

FIG. 3B is an axial section view of the device shown in FIG. 3A.

FIG. 3C is a side perspective view of the device shown in FIG. 3A, with the tubular member(s) slidably translated from the position shown in FIG. 3A.

FIG. 3D is an axial section view of the device configuration shown in FIG. 3C.

FIG. 4A is a side perspective view of a tubular drug containment system with a positive alignment mechanism according to embodiments of the present invention.

FIG. 4B is an end view of the tubular drug containment system shown in FIG. 4A with the inner and outer members rotated into a desired orientation according to embodiments of the present invention.

FIG. 4C is a side perspective view of a tubular drug containment system with a positive alignment mechanism according to embodiments of the present invention.

FIG. 4D is an end view of the tubular drug containment system shown in FIG. 4C with the inner and outer members slidably rotated into a desired orientation according to embodiments of the present invention.

FIGS. 5A-5H are axial section views of examples of different drug compartment configurations according to embodiments of the present invention.

FIG. 12A is an enlarged top perspective view of a drug containment system according to embodiments of the present invention.

FIG. 12B is an enlarged top perspective view of the device shown in FIG. 12A, illustrating the inner and outer members in a different position relative to each other according to embodiments of the present invention.

DESCRIPTION OF EMBODIMENTS OF THE INVENTION

Figure 1:
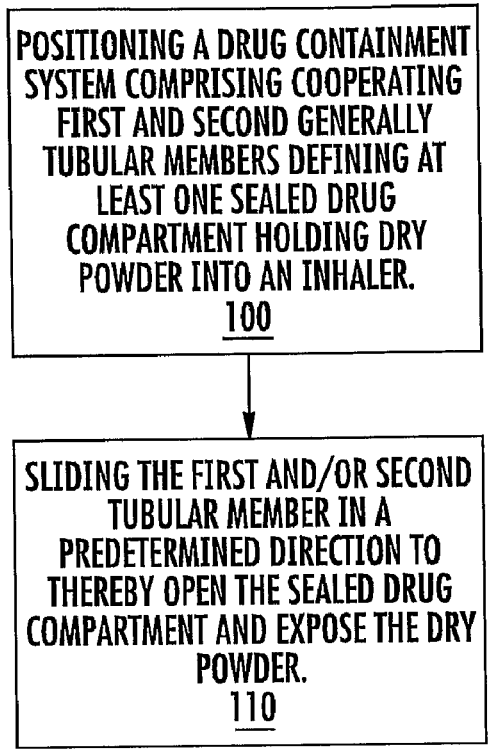

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. In the drawings, the thickness of lines, layers, features, components and/or regions may be exaggerated for clarity and broken lines illustrate optional features or operations, unless specified otherwise.

It will be understood that when a feature, such as a layer, region or substrate, is referred to as being "on" another feature or element, it can be directly on the other feature or element or intervening features and/or elements may also be present. In contrast, when an element is referred to as being "directly on" another feature or element, there are no intervening elements present. It will also be understood that, when a feature or element is referred to as being "connected", "attached" or "coupled" to another feature or element, it can be directly connected, attached or coupled to the other element or intervening elements may be present. In contrast, when a feature or element is referred to as being "directly connected", "directly attached" or "directly coupled" to another element, there are no intervening elements present. Although described or shown with respect to one embodiment, the features so described or shown can apply to other embodiments.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and this application and should not be interpreted in an idealized or overly formal sense unless expressly so defined herein.

In the description of the present invention that follows, certain terms are employed to refer to the positional relationship of certain structures relative to other structures. As used herein, the term "front" or "forward" and derivatives thereof refer to the general or primary direction that the dry powder travels as it is dispensed to a patient from a dry powder inhaler; this term is intended to be synonymous with the term "downstream," which is often used in manufacturing or material flow environments to indicate that certain material traveling or being acted upon is farther along in that process than other material. Conversely, the terms "rearward" and "upstream" and derivatives thereof refer to the direction opposite, respectively, the forward or downstream direction.

The term "drug container package" describes a disposable drug container device that holds at least one unitized, meted and/or bolus amount of a target drug or medicament and may be also known as a drug containment system ("DCS"). The term "sealant layer" and/or "sealant material" includes configurations that have at least one layer or one material; thus, such a phrase also includes multi-layer or multi-material sealant configurations.

The devices and methods of the present invention may be particularly suitable for holding a partial or bolus dose of particulate dry powder substances that are formulated for in vivo inhalant dispersion (using an inhaler) to subjects, including, but not limited to, animal and, typically, human subjects. The inhalers can be used for nasal and/or oral (mouth) respiratory inhalation delivery.

The dry powder substance may include one or more active pharmaceutical constituents as well as biocompatible additives that form the desired formulation or blend. As used herein, the term "dry powder" is used interchangeably with "dry powder formulation" and means the dry powder can comprise one or a plurality of constituents or ingredients with one or a plurality of (average) particulate size ranges. The term "low-density" dry powder means dry powders having a density of about 0.8 g/cm$^3$ or less. In particular embodiments, the low-density powder may have a density of about 0.5 g/cm$^3$ or less. The dry powder may be a dry powder with cohesive or agglomeration tendencies.

In any event, individual dispensable quantities of dry powder formulations can be a single ingredient or a plurality of ingredients, whether active or inactive. The inactive ingredients can include additives added to enhance flowability or to facilitate aeorolization delivery to the desired target. The dry powder drug formulations can include active particulate sizes that vary. The device may be particularly suitable for dry powder formulations having particulates which are in the range of between about 0.5-50 μm, typically in the range of between about 0.5 μm-20.0 μm, and more typically in the range of between about 0.5 μm-8.0 μm. The dry powder formulation can also include flow-enhancing ingredients, which typically have particulate sizes that may be larger than the active ingredient particulate sizes. In certain embodiments, the flow-enhancing ingredients can include excipients having particulate sizes on the order of about 50-100 μm. Examples of excipients include lactose and trehalose. Other types of excipients can also be employed, such as, but not limited to, sugars which are approved by the United States Food and Drug Administration ("FDA") as cryoprotectants (e.g., mannitol) or as solubility enhancers (e.g., cyclodextrine) or other generally recognized as safe ("GRAS") excipients.

"Active agent" or "active ingredient" as described herein includes an ingredient, agent, drug, compound, and composition of matter or mixture, which provides some pharmacologic, often beneficial, effect. This includes foods, food supplements, nutrients, drugs, vaccines, vitamins, and other beneficial agents. As used herein, the terms further include any physiologically or pharmacologically active substance that produces a localized and/or systemic effect in a patient.

The active ingredient or agent that can be delivered includes antibiotics, antiviral agents, anepileptics, analgesics, anti-inflammatory agents and bronchodilators, and may be inorganic and/or organic compounds, including, without limitation, drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system, and the central nervous system. Suitable agents may be selected from, for example and without limitation, polysaccharides, steroid, hypnotics and sedatives, psychic energizers, tranquilizers, anticonvulsants, muscle relaxants, anti-Parkinson agents, analgesics, anti-inflammatories, muscle contractants, antimicrobials, antimalarials, hormonal agents including contraceptives, sympathomimetics, polypeptides and/or proteins (capable of eliciting physiological effects), diuretics, lipid regulating agents, antiandrogenic agents, antiparasitics, neoplastics, antineoplastics, hypoglycemics, nutritional agents and supplements, growth supplements, fats, antienteritis agents, electrolytes, vaccines and diagnostic agents.

The active agents may be naturally occurring molecules or they may be recombinantly produced, or they may be analogs of the naturally occurring or recombinantly produced active agents with one or more amino acids added or deleted. Further, the active agent may comprise live attenuated or killed viruses suitable for use as vaccines. Where the active agent is insulin, the term "insulin" includes natural extracted human insulin, recombinantly produced human insulin, insulin extracted from bovine and/or porcine and/or other sources, recombinantly produced porcine, bovine or other suitable donor/extraction insulin and mixtures of any of the above. The insulin may be neat (that is, in its substantially purified form), but may also include excipients as commercially formulated. Also included in the term "insulin" are insulin analogs where one or more of the amino acids of the naturally occurring or recombinantly produced insulin has been deleted or added.

It is to be understood that more than one active ingredient or agent may be incorporated into the aerosolized active agent formulation and that the use of the term "agent" or "ingredient" in no way excludes the use of two or more such agents.

Examples of diseases, conditions or disorders that may be treated with embodiments of the invention include, but are not limited to, asthma, COPD (chronic obstructive pulmonary disease), viral or bacterial infections, influenza, allergies, cystic fibrosis, and other respiratory ailments as well as diabetes and other insulin resistance disorders. The dry powder inhalation may be used to deliver locally acting agents such as antimicrobials, protease inhibitors, and nucleic acids/oligionucleotides as well as systemic agents such as peptides like leuprolide and proteins such as insulin. For example, inhaler-based delivery of antimicrobial agents such as antitubercular compounds, proteins such as insulin for diabetes therapy or other insulin-resistance related disorders, peptides such as leuprolide acetate for treatment of prostate cancer and/or endometriosis and nucleic acids or oligonucleotides for cystic fibrosis gene therapy may be performed. See e.g. Wolff et al., *Generation of Aerosolized Drugs*, J. Aerosol. Med. pp. 89-106 (1994). See also U.S. Patent Application Publication No. 20010053761, entitled Method for Administering ASPB28-Human Insulin and U.S. Patent Application Publication No. 20010007853, entitled Method for Administering Monomeric Insulin Analogs, the contents of which are hereby incorporated by reference as if recited in full herein.

Typical dose amounts of the unitized dry powder mixture dispersed in the inhaler may vary depending on the patient size, the systemic target, and the particular drug(s). A conventional exemplary dry powder dose amount for an average adult is about 10-30 mg and for an average adolescent pediatric subject is from about 5-10 mg. A typical dose concentration may be between about 1-2%. Exemplary dry powder drugs include, but are not limited to, albuterol, fluticasone, beclamethasone, cromolyn, terbutaline, fenoterol, β-agonists (including long-acting β-agonists), salmeterol, formoterol, cortico-steroids and glucocorticoids. In certain embodiments, the administered bolus or dose can be formulated with an increase in concentration (an increased percentage of active constituents) over conventional blends. Further, the dry powder formulations may be configured as a smaller administerable dose compared to the conventional 10-25 mg doses. For example, each administerable dry powder dose may be on the order of less than about 60-70% of that of conventional doses. In certain particular embodiments, using the active dispersal systems provided by certain embodiments of the DPI configurations of the instant invention, the adult dose may be reduced to under about 15 mg, such as between about 10 μg-10 mg, and more typically between about 50 μg-10 mg. The active constituent(s) concentration may be between about 5-10%. In other embodiments, active constituent concentrations can be in the range of between about 10-20%, 20-25%, or even larger. In particular embodiments, such as for nasal inhalation, target dose amounts may be between about 12-100 μg.

In certain particular embodiments, during dose dispensing, the dry powder in a particular drug compartment or blister may be formulated in high concentrations of an active pharmaceutical constituent(s) substantially without additives (such as excipients). As used herein, "substantially without additives" means that the dry powder is in a substantially pure active formulation with only minimal amounts of other non-biopharmacological active ingredients. The term "minimal amounts" means that the non-active ingredients may be present, but are present in greatly reduced amounts, relative to the active ingredient(s), such that they comprise less than about 10%, and preferably less than about 5%, of the dispensed dry powder formulation, and, in certain embodiments, the non-active ingredients are present in only trace amounts.

Turning now to the figures, FIG. 1 illustrates that a drug containment system, comprising slidably cooperating first and second generally tubular members defining at least one sealed drug compartment holding dry powder, can be positioned in an inhaler (block 100). The first and/or second generally tubular member can slide in a predetermined direction to thereby open the sealed drug compartment and expose the dry powder (block 110). The first and/or second member can define the ceiling or floor of a respective drug compartment. Moving the first and/or second member a predetermined direction automatically opens (unseals) the drug compartment to expose the dry powder and allow the drug powder to enter the inhalation flow path. The first and/or second generally tubular member(s) can define an elongate portion of the inhalation flow path.

Figure 2:
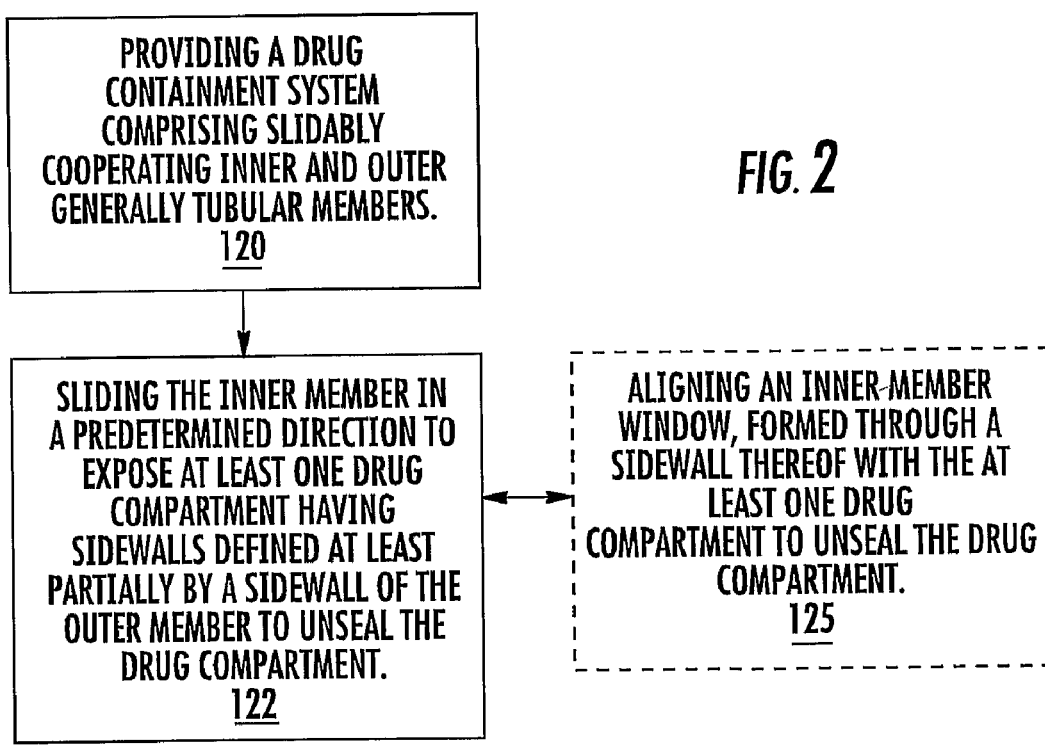

FIG. 2 illustrates that the first member can be an outer member and the second member can be an inner member (block 120). The inner member can slide in the predetermined direction to expose at least one drug compartment that has sidewalls defined, at least partially, by a sidewall of the outer member to unseal the drug compartment(s) (block 122). Optionally, the inner member can have a window that extends through a wall thereof and the window can be aligned with the drug compartment providing the opening for the dry powder into a flow path defined by the inner member (block 125). In other embodiments, the inner member can have an axial length that, in operative position, terminates before the underlying drug compartment to open the drug compartment.

The term "generally tubular" means that the so-described component can have an elongate body with a generally hollow elongate interior passage, but that the cross-sectional shape of the body is not limited to circular shapes. The cross-sectional shape may be generally circular, oval, elliptical, square, rectangular, triangular, or other geometric shape. The wall(s) of the tubular member can be uniform or non-uniform. In some embodiments, two or more nested generally tubular members of graduated size can be configured to snugly fit together, one inside the other. The nested members can have a common axial center-line. The nested members can have a common cross-sectional shape that is constant or varies along its length. Typically, the nested configuration is such that the first and second members snugly abut each other and at least one of the members is configured to slide relative to the other.

Figure 3A:
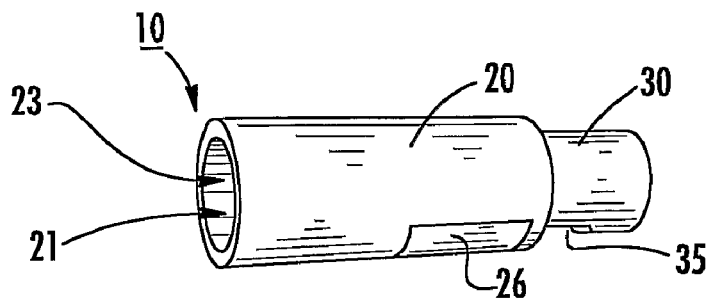
Figure 3B:
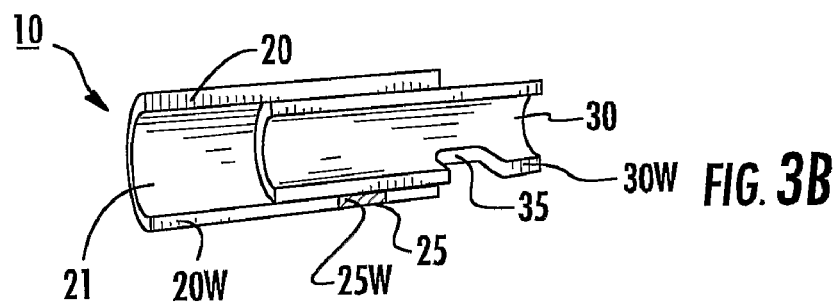
Figure 3C:
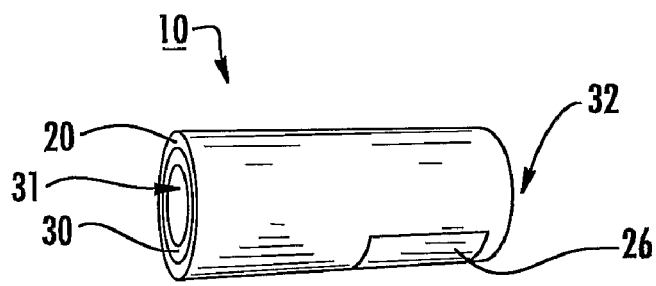
Figure 3D:
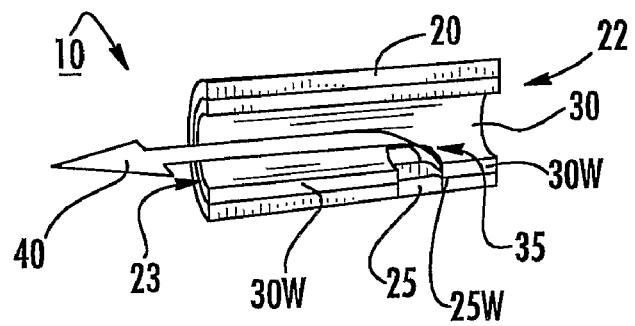

FIGS. 3A-3D illustrate an exemplary drug containment system 10 with a tube in tube (i.e., nested tubular member) embodiment that has at least one sealed drug compartment 25 (FIG. 3B). The system 10 includes an outer member 20 and an inner member 30. The outer member 20 is sized and configured to snugly and slidably receive the inner member 30. FIGS. 3A and 3B illustrate the inner member 20 having a first "closed" configuration relative to the outer member 20. As shown, the inner member 30 defines a closed surface (shown as a ceiling in this embodiment) over the drug compartment 25, thereby providing a sealed drug compartment that traps the drug (typically a dry powder inhalant drug) therein. FIGS. 3C and 3D illustrate the inner member 20 in a second "open" configuration. As shown, the inner member 30 has a window 35 extending through a wall 30w thereof. Sliding the inner (and/or outer) member 30 so that the window 35 is aligned above the drug compartment 25 removes the ceiling and opens the drug compartment 25 to expose the drug and release the drug for inhalation. The inner member 30 can define at least an elongate portion of the flow path 40.

The outer member 20 can have at least one aperture 20a formed into a wall 20w of the outer member 20. In some embodiments, as shown in FIGS. 3A and 5A, the aperture 20a extends through the wall 20w of the outer member 20 and an outer layer 26 (floor or ceiling layer, depending on the orientation of the drug compartment 25) can be attached to seal the outside of the drug compartment 25. In other embodiments, as shown in FIG. 5E, the aperture 20a can terminate a distance within the wall of the outer member 20 so that the outer member 20 defines the outer surface of the drug compartment 25.

Thus, the drug compartment 25 can have sidewalls 25w that are defined at least partially by the thickness of the outer member 20. In particular embodiments, as shown in FIG. 3B, the sidewalls 25w of the sealed and/or closed drug compartment 25 are defined by the thickness of the outer member 20. The outer layer 26 can be a thin, planar sealant floor layer as shown. In other embodiments, the outer layer 26 can be non-planar (not shown). The outer layer 26 can be moisture-resistant and pharmaceutically compatible. The outer layer 26 can comprise a polymer. In operation in an inhaler, as will be discussed further below, a vibrator can be in communication with the drug compartment 25 and/or the outer layer 26. In some embodiments, as will also be discussed further below, the outer layer 26 comprises a piezoelectric film material, typically a polymer such as PVDF (known as KYNAR® piezo film or polyvinylidene fluoride).

The inner member 30 can have about the same thickness as the outer member 20. The inner member thickness can provide additional sidewall depth/thickness when the inner member window 35 is aligned with the outer member aperture. The inner member 30 may also have a greater or lesser thickness than the outer member 20. In addition, in some embodiments, the inner member 30 has a shorter length than that of the outer member 20 and, in operative position, may terminate a distance downstream or upstream of the exit port 23 (FIGS. 5F-5H) of the drug containment system 10. In other embodiments, such as shown in FIGS. 3A and 3D, in the open configuration, the inner member 30 can be generally flush with the end of the outer member 20, or, as shown in FIG. 5G, the inner member 30 can extend beyond the outer member 20 to provide the exit port 23.

The inner member window 35 can be substantially the same shape and size as the outer member aperture 20a. In other embodiments, the inner member window 35 can be larger and/or longer than the aperture 20a. Alternatively, the inner window 35 can be smaller or shorter than the outer member aperture 20a. As shown in FIG. 5A, the window 35 can have at least a length "L" that can span over a plurality of proximate drug compartments 25, which combined have an axial length "L". Alternatively, or additionally, the inner member 30 can extend over and/or under a plurality of drug compartments 25. To that end, the inner member 30 can be a unitary member that is devoid of apertures (FIGS. 5G-5H) or can include a plurality of (axially, radially and/or circumferentially) spaced apart windows 35 that reside over or under a plurality of drug compartments 25. FIG. 5D illustrates that the inner member 30 can include generally diametrically opposed (circumferentially spaced apart) windows 35 that can concurrently open and seal circumferentially spaced apart drug compartments 25. Other arrangements of windows 35 and/or drug compartments 25 may be used.

For some multiple drug compartment embodiments, a combination delivery can be employed using in situ mixing of different drugs that held in drug compartments that are opened by moving the outer and/or inner member 20, 30 to allow the drugs to mix and be inhaled concurrently. In particular embodiments, as shown for example in FIG. 5D, rotating the inner tube 30 can open a drug in a top compartment 25 and a bottom compartment 25. The drug in the top compartment can fall into or proximate the bottom compartment where each drug can be dispersed.

As shown in FIGS. 3A-3D, the inner member 30 includes generally open opposing ends 31, 32 that define an elongate portion of the inhalation drug delivery flow path 40 (FIG. 3D) in the inhaler. Similarly, the outer member 20 can also have generally open ends 21, 22 particularly the end that slidably receives the inner member 30.

FIGS. 4A and 4B illustrate that the outer and inner members 20, 30, respectively, can be configured to facilitate proper positive dispensing orientation of the drug compartment 25. That is, the outer member 20 can include a slot 21 and the inner member 30 a tab 30t or key that is configured to enter therein to positively align the inner member relative to the outer member 20, 30. The reverse configuration may also be used (i.e., with the slot on the inner member and the tab or key on the outer member) as well as other positive positioning mechanisms. Further, the outer member 20 can include a second slot 22 that engages with a key or tab in an inhaler to facilitate proper dispensing orientation in the inhaler. As before, the reverse configuration and/or other positive orientation mechanisms can be used.

FIGS. 4C and 4D illustrate that the outer and inner members 20, 30 can be configured to positively control a rotation direction and distance using a circumferentially formed slot 20s and tab 30t. The rotation-guide slot 20s can be positioned at any desired location on the outer member 20. In some embodiments, as shown in FIG. 4C the outer member 20 may optionally include both an axial and circumferential slot 20s that merge. The reverse configuration may also be used (i.e., with the slot on the inner member and the tab or key on the outer member) as well as other positive positioning mechanisms. Further, the outer member 20 can include the second slot 22 shown in FIG. 4A that engages with a key or tab in an inhaler to facilitate proper dispensing orientation in the inhaler. As before, the reverse configuration and/or other positive orientation inhaler/system mechanisms can be used.

Figure 5F:
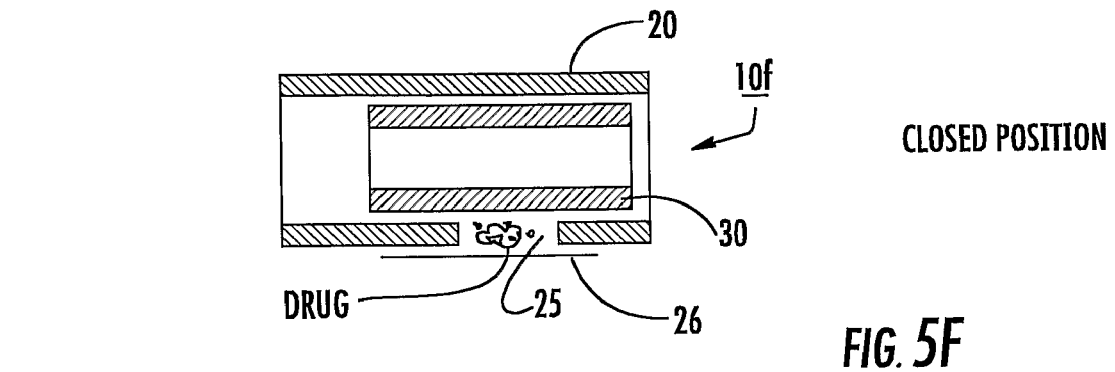
Figure 5G:
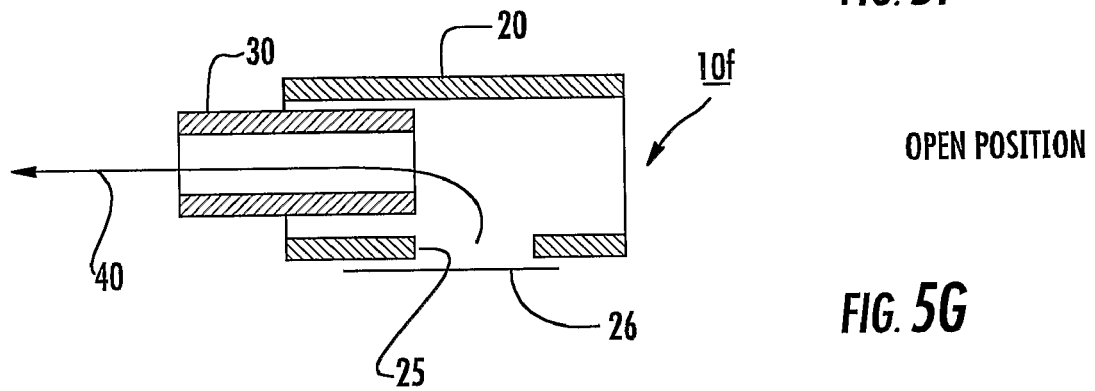

FIGS. 5A-5H illustrate some exemplary configurations of a drug containment system 10 (identified as 10a-10f for ease of discussion). FIG. 5A illustrates that the system 10a can include a plurality of axially spaced apart drug compartments 25. FIG. 5A also illustrates, similar to FIGS. 3A-3D, that the inner member 30 can slidably advance to open the drug compartment(s) 25. Alternatively, the outer member 20 can slide relative to the inner member 30. In some embodiments, the inner 30 or outer member 20 can slidably retract. FIG. 5B illustrates a system 10b with the inner member 20 and/or outer member 30 rotatable to position the window 35 proximate the drug compartment 25. The members 20, 30 can be configured to both slidably rotate and slide axially or to only rotate when in the inhaler (FIGS. 5B and 4C). In some embodiments (as shown in FIGS. 3A and 4A), the system 10 is configured to slide only axially. In other embodiments, the system 10 can be configured so that the members 20, 30 only rotate.

Depending on the application, in operative position, the drug compartment 25 can be held above the flow path 40 or below (typically below and generally orthogonal to the flow path as shown in FIG. 3D). FIG. 5C illustrates a system 10c with an outer member 27 that can extend beyond the bounds of the outer member body (extending outwardly therefrom a desired distance) to provide a deeper drug compartment 25. The outer member 27 can be rigid or be in the form of a resilient blister. In some embodiments the sidewalls 27w of the outer member 27 are generally rigid, and the outer surface 27s can be of the same material or comprise a planar flexible sealant layer as described for the embodiment shown in FIG. 3A.

FIG. 5D illustrates a system 10d with diametrically opposed drug compartments $25_1$, $25_2$, typically positioned generally orthogonal to the flow path 40 (FIG. 3D) and/or axial centerline 41. FIG. 5E illustrates that the system 10 can be configured so that the drug compartment floor or ceiling surface 25s (shown as a floor in the orientation shown in FIG. 5E) is defined by the outer member 20.

Figure 5H:
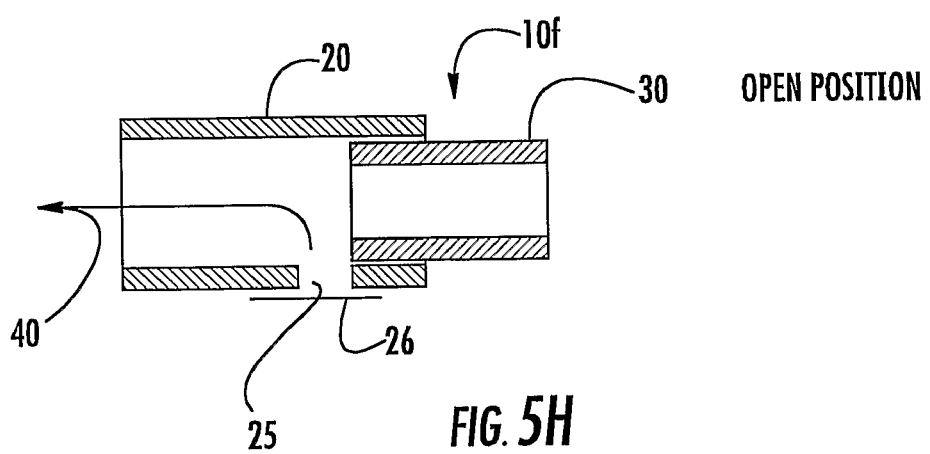

FIGS. 5F-5H illustrate a drug containment system 10f having an inner member 30 with a continuous wall (i.e., be a unitary member that is devoid of apertures). To open one or more drug compartment(s) 25, the inner member 30 can move forward (FIG. 5G) or rearward (FIG. 5H). The drug compartment 25 may include an outer layer 26 or the outer member 30 can provide the sidewalls and outermost surface (ceiling or floor) of the drug compartment (FIG. 5E).

The drug containment system 10 can be single-use disposable. The inner and outer members 30, 20, respectively can comprise a lightweight generally rigid material. The member 30 includes a plurality of spaced apart cavities or wells 25w. The members 20, 30 can comprise a generally rigid elastomeric material. The phrase "generally rigid" means that the body may flex somewhat but is structurally sufficiently rigid to maintain its shape when the other components are assembled thereto. The members 20, 30 may be configured with sufficient thickness, material and/or coatings to provide a moisture barrier (inhibit moisture penetration) to the dry powder held in the drug compartment 25.

In some embodiments, the outer and inner members 20, 30 can comprise a polymer and/or copolymer and/or derivatives thereof, such as, for example, a high-density polyethylene material. The drug containment system 10 can have a length that is between about 10-75 mm, typically between about 30-50 mm, and, in some embodiments, about 40 mm. The inner member 30 and outer member 20 can be sized and configured to frictionally slidably engage. In some embodiments, the inner member 30 can have an inner diameter that is about 6 mm, and outer diameter or thickness that is about 8 mm. The outer member 20 can have an inner diameter or thickness of about 10 mm in segment 1 ($20_1$, FIG. 14) proximate the drug well 25 (FIG. 3A) with an outer diameter of about 11-15 mm. The dimensions can vary.

As shown in FIGS. 3A and 5A-5D, the layer 26 resides on an outermost surface of the outer member 20 and typically extends at least the length of a respective drug compartment(s) 25, with an axial length of between about 6.35-50.8 mm (about 0.25-2 inches), typically less than about 25.4 mm (1 inch), and more typically about 12.7 mm (about ½ inch).

Figure 6:
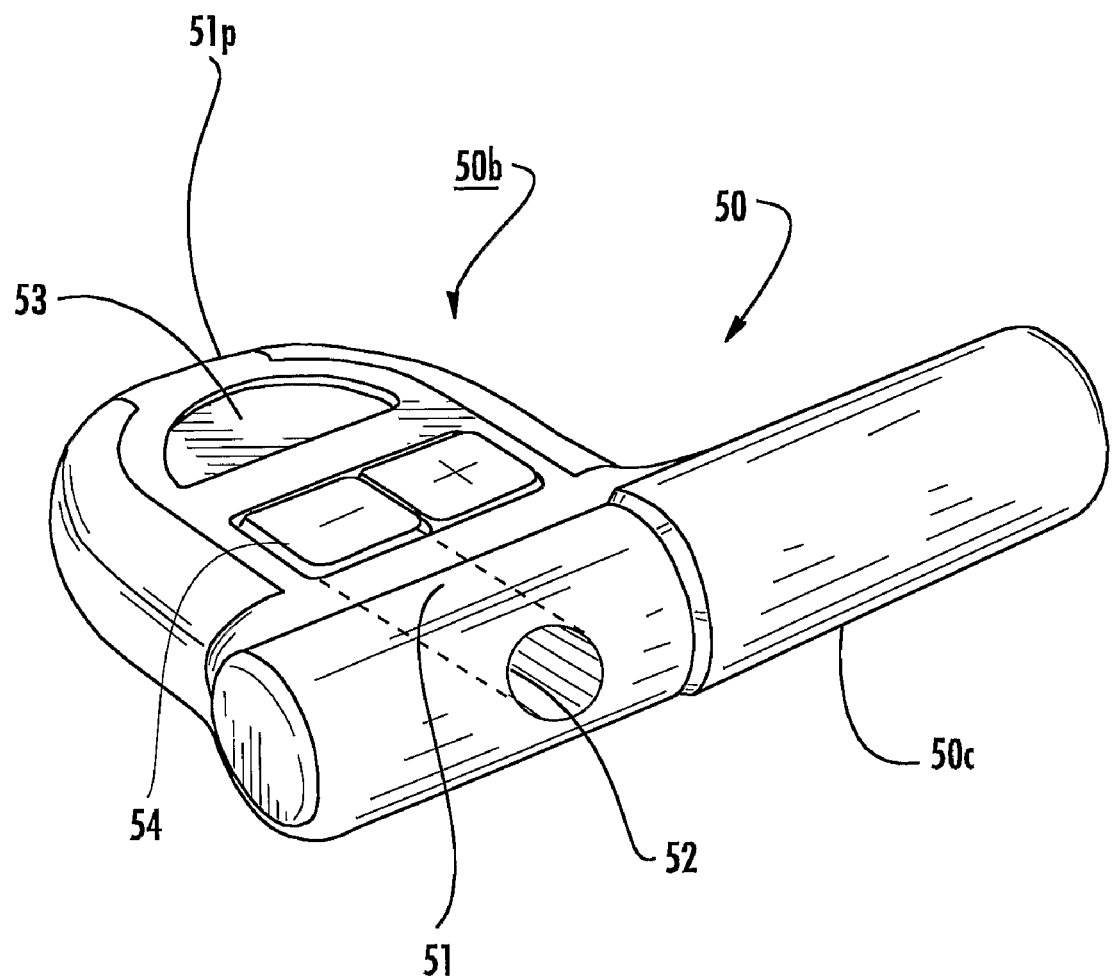
FIG. 6 is a side perspective view of an inhaler according to embodiments of the present invention.

FIG. 6 illustrates an inhaler 50. The inhaler 50 can include an elongate channel 51 that is sized and configured to receive the generally tubular drug containment system 10 therein. The channel 51 can include a port 51p that is in fluid communication with the airflow path 40 (FIG. 3D) of the system 10. In position, in some embodiments, the system 10 cooperates with the inhaler channel 51 to provide input of external air via port 51p into the flow path 40 in the inhaler 50 to the mouthpiece 52. In operation, the system 10 can be inserted into the inhaler 50. The inhaler 50 can include a mechanism that automatically contacts the inner 30 and/or outer member 20 upon insertion and slides the member(s) in a predetermined direction(s) to open the at least one drug compartment 25 (FIGS. 3A and 5A-5D).

As shown in FIG. 6, the inhaler 50 also includes a mouthpiece port 52 in fluid communication with a properly positioned system 10 whereby a user can inhale the dry powder or other drug therefrom. A sliding dust cover 50c can laterally (in a direction generally orthogonal to the flow channel 40) extend and retract to expose and cover the mouthpiece port 52. Other cover configurations may be used.

Figure 7A:
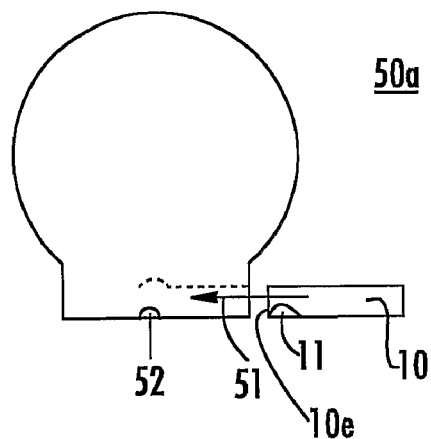
FIGS. 7A-7D are top schematic views of an inhaler with alternate loading configurations according to embodiments of the present invention.
Figure 7B:
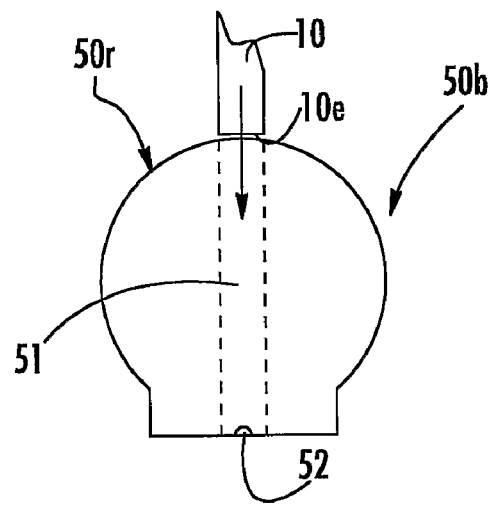
Figure 7C:
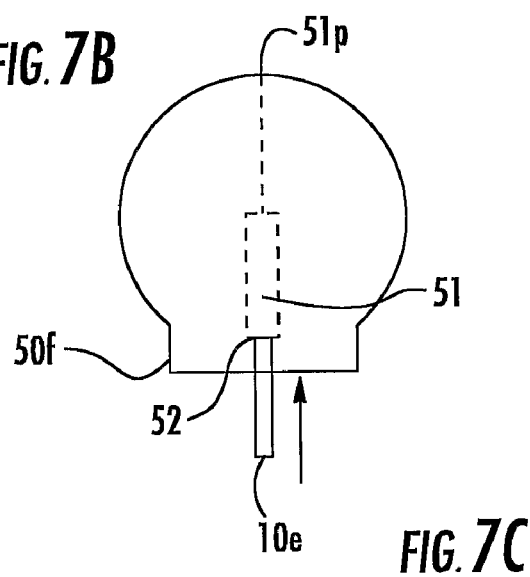

FIGS. 7A-7D illustrate examples of drug containment system loading configurations in the inhaler 50. FIG. 7A illustrates that the system 10 can be loaded from a side entry into the inhaler 50. A forward portion of the system 10 can be configured to reside proximate the mouthpiece port 52 when in proper position in and/or on the inhaler 50. The forward portion of the system 10e may include a sidewall port 11 or other flow configuration that can align with the mouthpiece port 52 to direct the dry powder out of the inhaler 50. FIG. 7B illustrates that the system 10 can be inserted from a rear portion of the inhaler 50r into the channel 51. FIG. 7C illustrates that the system 10 can be inserted from a forward portion 50f (defined as the location facing the user in operative position) of the inhaler 50.

The drug containment system 10 can be inserted a distance into the inhaler 50 so that the system leading edge 10e extends out a distance beyond the port 52. In other embodiments, the system 10 can reside entirely in the inhaler 50, the leading edge portion 10e being generally flush or recessed therein. When the leading edge 10e extends beyond the bounds of the inhaler 50, the drug containment system 10 can define the mouthpiece or patient contact region inhale port. In this manner, the drug containment system 10 provides a disposable inhalation flow path that inhibits drug residue from doses over time from being trapped or residing in the inhaler flow path. Other loading configurations may be used.

Figure 7D:
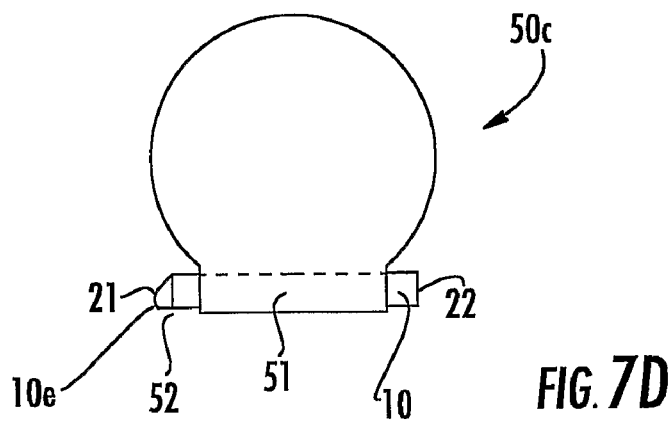

In some embodiments, the drug containment system 10 defines the air inlet port 52 as shown in FIG. 7D. In some embodiments, the mouthpiece port 52 and the air inlet port 51p are spaced apart about a distance of between about 51-127 mm (about 2-5 inches), and typically between about 76.2-101.6 mm (about 3-4 inches). The body 50b can have a portable relatively compact "pocket-sized" configuration. In some embodiments, the body 50b can have a width/length that is less than about 115 mm (about 4.5 inches), typically less than about 89 mm (about 3.5 inches), and a thickness/depth of less than about 51 mm (about 2 inches), typically less than about 38 mm (about 1.5 inches). The inhaler body 50b can also be configured to be generally planar on opposing primary surfaces to facilitate pocket storage.

The inhaler 50 can also include a display 53 and a user input 54. The user input 54 shown includes a "+" and a "−" input key. The user input 54 can comprise contact pads, a touch screen or other input means, including a numeric entry device which can be used to track the amount of unitized bolus amounts of a target bolus amount of a drug needed by a user as will be discussed further below.

In some embodiments, unlike conventional inhalers, the inhaler 50 can be configured to allow a user to electronically input a variable target unitized bolus amount. The term "unitized" means a specified quantity of a pharmaceutical drug and/or medicament in terms of which the magnitudes of other quantities of the same or different drug and/or medicament can be stated. Thus, particularly where a user will need to dispense medication from more than one vial or delivery system 10, the display 53 can be configured to help a user determine/remember what has been dispensed and/or what remains to be dispensed to meet the target bolus amount.

Such practices differ from conventional drug delivery, in which a user typically takes the same bolus based on a dispensed prescription irrespective of the physiological condition of the user at a particular time (i.e., one or two capsules or pills) or 1-2 "puffs". Instead, a user may have disease that would benefit from administration of a contemporaneously adjustable unitized dose based on the condition of the user at that time. The inhaler 50 can allow the user to increment (via the "+" key") and/or decrement (via the "−" key) the display 53 (FIG. 6) to identify in situ a target bolus number to the bolus amount then-needed. For example, a diabetic can take a blood or other body measurement that can be used to determine a target unitized bolus amount of medicament needed proximate in time to the measurement.

The drug(s) can be packaged in different unitized amounts in different drug containment systems 10, all of which can be dispensed from the inhaler 50. The different unitized amounts may be provided in a plurality of different unitized amounts, typically between 1-10. In some embodiments, the unitized amounts can be provided as at least three different selectable amounts, such as "1", "3" and "4". The different unitized amounts may be identified by external indicia, such as drug containment system labeling, color, and or tube size. For example, each different unit size system 10 can have a different color (such as blue, yellow, green, and the like). In particular embodiments, the inhaler can display a corresponding color to allow the user to select the correct system 10 for dispensing. That is, for a unitized dose of "3" which is held in a blue system 10, the display can display a blue light or a blue icon that helps a user select the proper system 10. The drug containments systems 10 can include electronically and/or optically readable data that identifies one or more of the unitized amount associated therewith and the type of medicament therein.

The inhaler 50 can be programmed to inhibit operation if an incorrect medicament type and/or amount is placed therein. For example, the inhaler and/or generally tubular system 10 can be configured with a lockout mechanism (electronic or electromechanical) that can prevent operation of the inhaler to prevent the inhaler from dispensing a non-prescribed medication or drug. In addition, the inhaler and/or system 10 can be configured to inhibit reuse of the generally tubular system 10. That is, as it is contemplated that the system 10 will be single-use disposable, to inhibit the improper reuse and/or potential dispensing of illegal narcotics, the inhaler can be configured to electronically disable reuse of the system 10. The anti-misuse feature can be configured so that the system 10 can be automatically mechanically deformed or electronically disabled after dispensing its target contents. Further, the inhaler can be a smart-inhaler that can electronically verify the weight of the system 10, time of the previous dispensing (to inhibit overuse), as well as predetermined electronic data held on the container system 10, and the like, before allowing operation.

Figure 8:
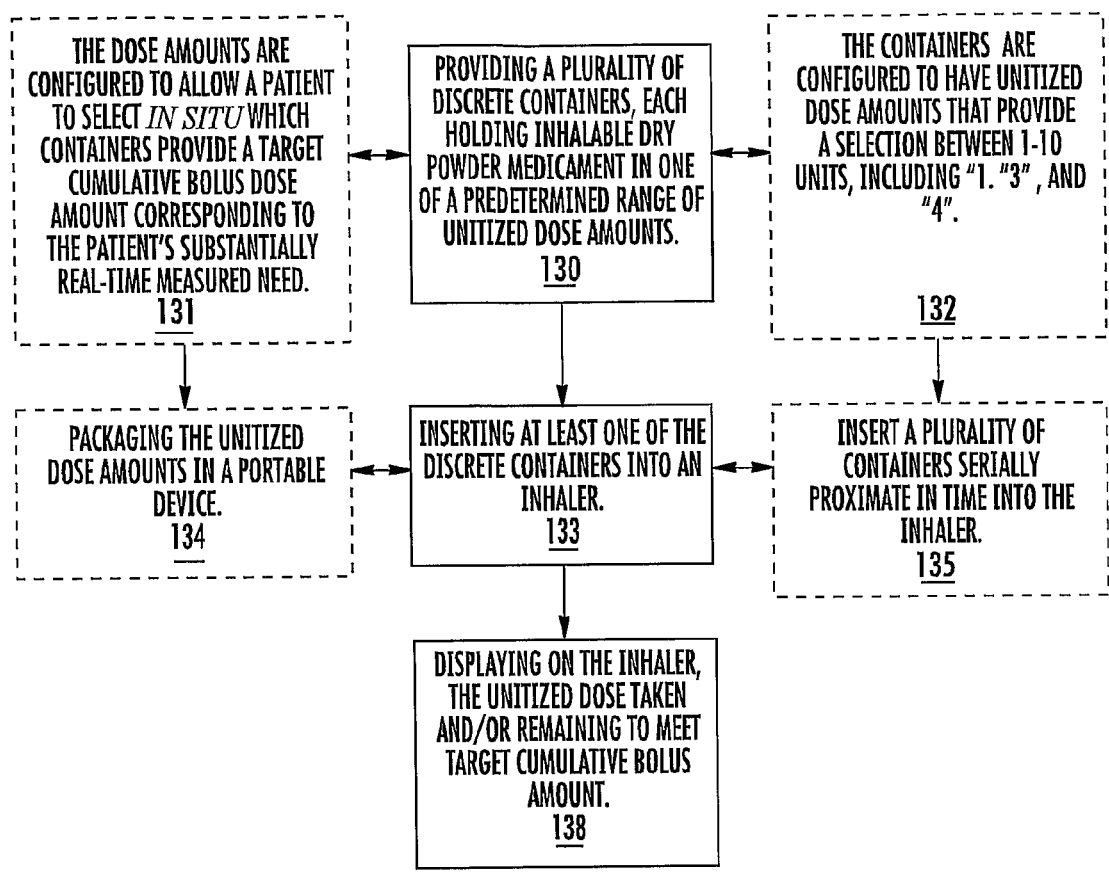
FIG. 8 is a flow chart of operations that can be used to administer a desired bolus of inhalant medication according to embodiments of the present invention.

FIG. 8 illustrates some operations that can be carried out according to embodiments of the present invention. A plurality of discrete containers can be provided (or packaged), each discrete container holding a unitized amount of inhalable dry powder medicament in one of a predetermined range of unitized dose amounts (block 130). At least one of the discrete containers is selectably inserted into the inhaler (block 133). The inhaler displays the unitized dose taken and/or the remaining dose amount needed to meet the target cumulative bolus amount (block 138).

In some embodiments, the containers have unitized dose amounts that provide a selection of unitized amounts, typically between 1-10 units, including containers with "1", "3" and "4" units (block 132). At times, the user can insert a single container to meet the bolus amount while at others, a plurality of the containers will be serially inserted for inhalation delivery (block 135). The dose amounts can be configured to allow a patient to select in situ which containers provide the target cumulative bolus amount corresponding to the patient's substantially real time measured need (block 131). The containers can be packaged in a portable device holding the different unitized dose amounts (block 134).

Figure 9:
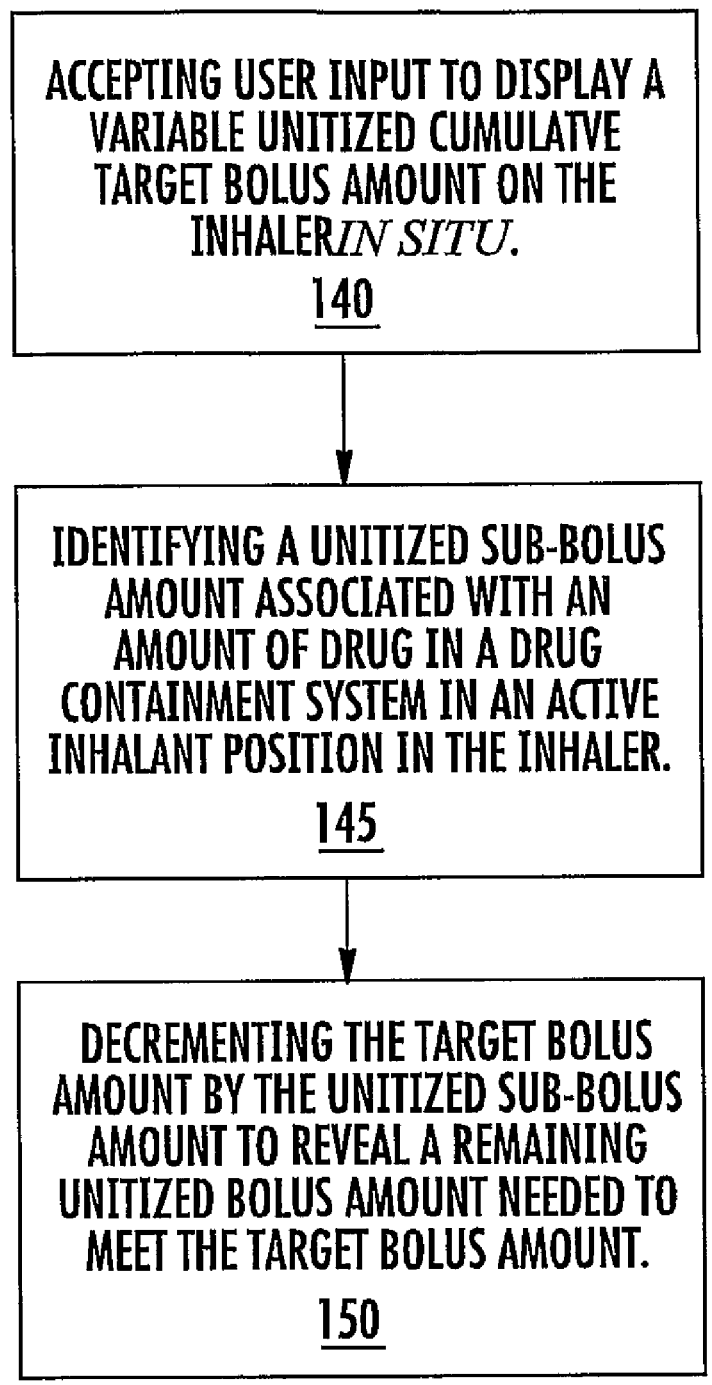
FIG. 9 is a flow chart of inhaler operations that can be used to track a desired unitized bolus amount of an inhalant medicament according to embodiments of the present invention.

FIG. 9 illustrates operations that can be carried out using an inhaler to provide an inhalation medicament. User input can be accepted in situ to display a (variable) unitized cumulative target bolus amount (block 140). A unitized sub-bolus amount can be identified associated with an amount of drug in a drug containment system positioned in an active delivery position in the inhaler can be identified (block 145). The target bolus amount on the inhaler display can be decremented by the unitized sub-bolus amount to reveal a remaining unitized bolus amount needed to meet the target bolus amount (block 150).

Figure 10A:
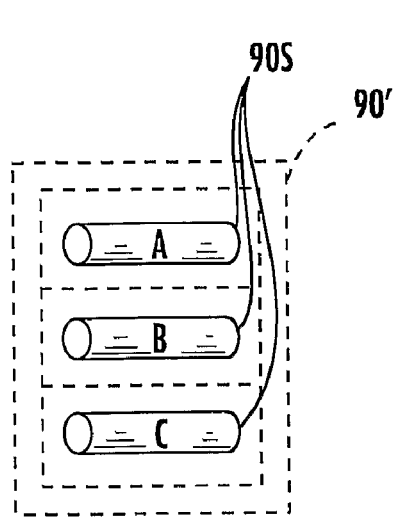
FIGS. 10A-10C are schematic illustrations of packaged kits of different unitized dose amounts of inhalant drugs that can be dispensed in a common inhaler according to embodiments of the present invention.
Figure 10B:
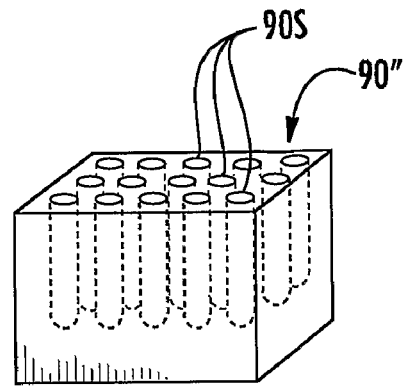
Figure 10C:
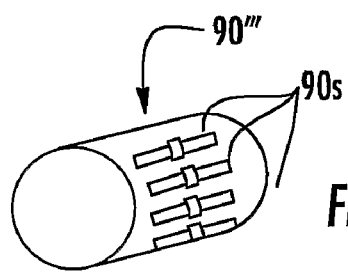
Figure 10D:
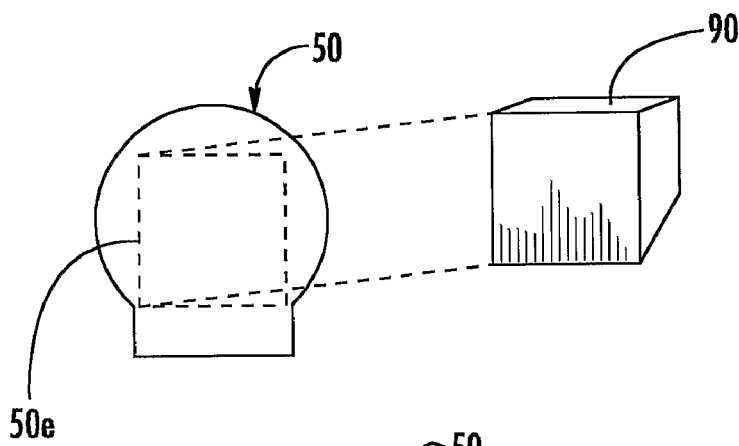
FIG. 10D is a schematic exploded illustration of a portable supply of drug containment systems that can be held by an inhaler according to embodiments of the present invention.
Figure 10E:
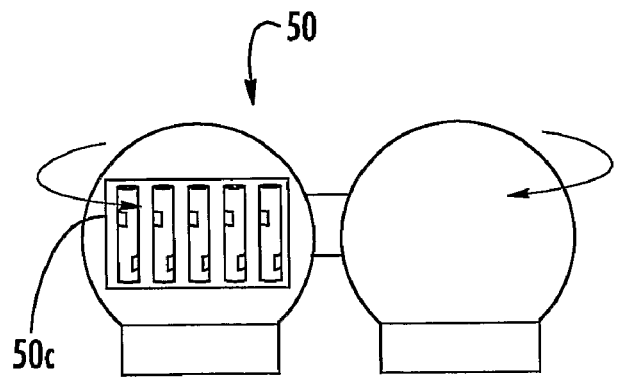
FIG. 10E is a schematic top view of an inhaler that includes an internal storage compartment for providing a portable supply of drug containment systems according to other embodiments of the present invention.

FIGS. 10A-10C illustrate exemplary portable packages 90 of a set 90s of different unitized drug containment systems 10. FIG. 10A illustrates that a package can be dispensed in at least three different unitized amounts (amounts A, B and C). Each can be separately packaged in biocompatible sterile packaging and then packaged in a set 90s. FIG. 10B illustrates that the containers 10 can be held in a package 90" that is relatively dense generally vertically-oriented array, with each row or column providing a different unitized amount. FIG. 10C illustrates that the containers 10 can be held in an arm, wrist, leg or ankle band 90''' for portable access. FIG. 10D illustrates that the package 90 can be configured to releasably mount on an external portion of the inhaler 50e (typically an underside) for portable access. FIG. 10E illustrates that the inhaler 50 can pivot open to define a holding chamber 50c therein for portable access to the unitized dose containers 10. Other peripheral and/or integral portable container supply configurations may also be used.

In some embodiments, the inhaler 50 can include an electronic sensor 75 (FIG. 11B) that interfaces with the system 10 when positioned in and/or on the inhaler 50 and can automatically adjust the cumulative bolus amount shown on the display by the sub-bolus amount of a drug containment system 10 in the inhaler after successful inhalation thereof. Similarly, the drug containment system 10 can include electronic media, such as electronic memory, a microchip, or optical or other electronic indicia that can be automatically interrogated by the sensor 75 (FIG. 11B) and/or a reader operatively associated with the inhaler 50 and the data relayed to a controller upon input into the inhaler.

Figure 11A:
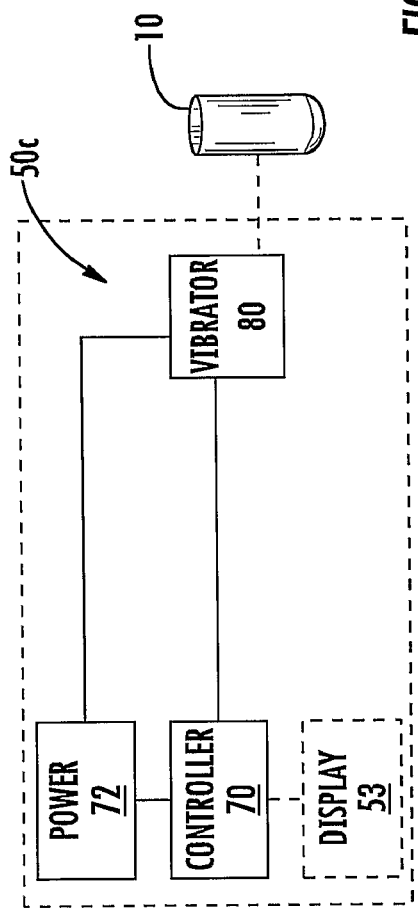
FIGS. 11A and 11B are schematic circuit block diagrams of exemplary inhaler operating circuits according to embodiments of the present invention.
Figure 11B:
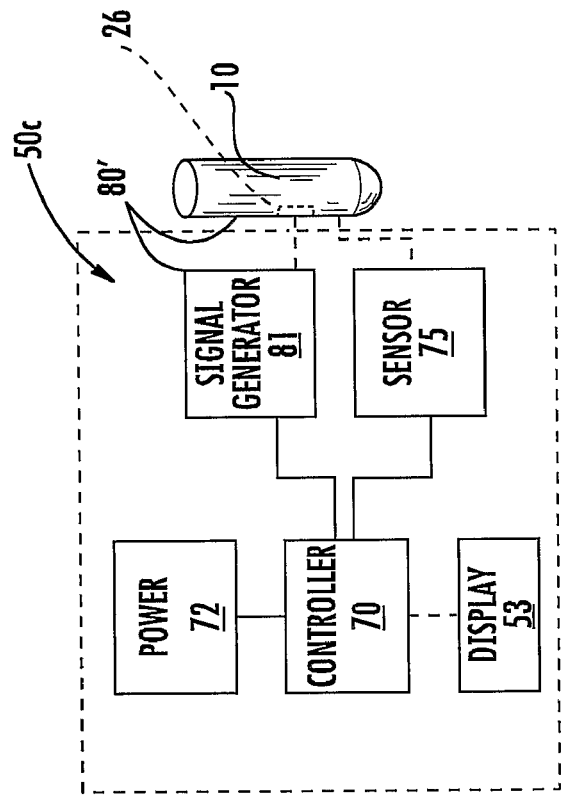

As shown in FIGS. 11A and 11B, the inhaler 50 can include a circuit 50c that controls certain operations of the inhaler 50. The circuit 50c can include a power source 72 and a controller 70 that can automatically decrement the displayed number on the display 53 after an active inhalation delivery. As shown in FIG. 11B, the controller 70 may, in some embodiments, control the activation of a vibrator 80 that is in communication with the drug containment system 10 to promote release and/or fluidization of the dry powder during inhalation drug delivery.

The inhaler 50 can also be configured to be able to electronically communicate with a remote location or device and/or provide additional data. The inhaler 50 can be configured with a clock and can generate patient alarms, alerts and/or reminders to take the medicine or evaluate whether a medicine is desired at target intervals or (selectable) times. The inhaler 50 can be configured to provide an "on" and/or "off" status indicator and/or generate one or more of: (a) a low battery charge warning; (b) a drug (over or under bolus) warning; and/or (c) a confirmation that the drug powder was successfully delivered (the above may be provide either via a visual and/or audible signal).

The inhaler 50 can include a computer port (not shown). The port may be, for example, an RS 232 port, an infrared data association (IrDA) or universal serial bus (USB), which may be used to download or upload selected data from/to the inhaler to a computer application or remote computer, such as a clinician or other site. The inhaler 50 can be configured to communicate with a clinician or pharmacy for refills and/or patient compliance. The inhaler 50 may also include a second peripheral device communication port (now shown).

In some embodiments, the controller 70 can include computer program code and/or computer applications that communicate additional data to a user (optionally to the display) as noted above and/or communicate with another remote device (the term "remote" including communicating with devices that are local but typically not connected during normal inhalant use) device.

In some embodiments, the controller 70 can be in communication with a signal generator as shown in FIG. 11B. The controller can be programmed with or in communication with an electronic library of a plurality of desired dry powder excitation signals that can be automatically selected by the controller 70 based on the data relayed and carried by the drug containment system 10 corresponding to the drug type/drug disposed therein. In this way, customized drug signals can be used to fluidize the dry powder. In other embodiments, the dry powder excitation signal can be carried on the electronic memory (not shown) held on the drug containment system 10 itself, and the controller 70 can be configured to output the signal to a vibrator 80 operatively associated with the dry powder. Examples of suitable excitation signals are described in co-pending U.S. Patent Application Publication Nos. 2004-0025877-A1 and 2004-0123864, the contents of which are hereby incorporated by reference as if recited in full herein. For example, the excitation signals can be powder specific and employ a carrier frequency modulated by one or more (amplitude) modulating frequencies that can facilitate fluidic and reliable flow of the dry powder.

The vibrator 80 can be any suitable vibrator configuration. The vibrator 80 can be configured to vibrate the tubular container 10. In some embodiments, the vibrator 80 can be configured to vibrate the drug compartment holding the dry powder. Examples of vibrators include, but are not limited to, one or more of: (a) ultrasound or other acoustic or sound-based sources (above, below or at audible wavelengths) that can be used to instantaneously apply non-linear pressure signals onto the dry powder; (b) electrical or mechanical deflection of the sidewalls and/or floor of the inhalation flow channel and/or drug compartment, which can include (electro) magnetic caused vibrations and/or deflections; (c) solenoids, piezoelectrically active portions and the like; and (d) oscillating or pulsed gas (airstreams), which can introduce changes in one or more of volume flow, linear velocity, and/or pressure. Examples of mechanical and/or electromechanical vibratory devices are described in U.S. Pat. Nos. 5,727,607, 5,909,829 and 5,947,169, the contents of which are incorporated by reference as if recited in full herein. In some particular embodiments, the vibrator 80 includes at least one piezoelectric element, such as a piezoceramic component, and/or a piezoelectric polymer film. In the circuit 50*c* shown in FIG. 11B, the vibrator 80' can comprise a signal generator 81 held in the inhaler 50 and a piezoelectric member (shown as piezoelectric film 26) held on the tubular container 10. An example of a suitable piezoelectric vibrator 80' will be discussed further below.

In particular embodiments, as discussed above, the drug compartments 25 can be closed on one side by a sealant material 26, shown as a floor in the embodiment shown in FIG. 3A. Meted and/or bolus amounts of dry powder can be disposed in the drug compartments and sealed in the drug compartment via the sealant material 26. The sealant material 26 can comprise foil, TEDLAR, or other moisture resistant barrier material. The sealant material 26 can be configured as a thin, flexible and/or resilient film. For example, the sealant material 26 can contain foil (such as aluminum or other suitable material) and/or may be a laminated structure, comprising a polymer layer and a foil layer. In particular embodiments, the sealant 26 can comprise layers of polyamide film, aluminum foil, and polypropylene film (where the top layer may be the polyamide film) adhered to each other with a laminating adhesive. In certain embodiments, the sealant 26 can have a thickness of between about 0.100-0.150 mm, and typically about 0.127 mm.

As will be discussed further below, turbulence promoters can be positioned in the flow path to promote turbulent flow. The turbulence promoters can be disposed downstream of a drug compartment(s) 25. For example, the flow path 40 (FIG. 3D) can include one or more of tabs, fingers, and/or a flow path geometry that can promote turbulence, and may slow the powder flow as it approaches and/or exits the inhaler 50 at the mouthpiece port 52 (FIG. 6), while reducing any dry powder trapping, can be used (not shown).

In some embodiments, translating the cover to an open or closed position 50*c* (FIG. 6) can optionally turn the inhaler 50 "on" and/or "off". The cover 50*c* can be moved into operative position manually and/or electronically. In some embodiments, the movement of the cover 50*c* can electronically initiate a priming or pre-vibration of the drug containment system 10 in the inhaler 50. This vibration can help shake the dry powder off the inner surfaces of the drug compartment 25. The vibration can be carried out in any suitable manner as discussed above.

As described above, in some embodiments, the system 10 can be operatively associated with a (piezoelectric) vibrator 80' (FIG. 11B) to promote fluidic flow of the dry powder during inhalation. In some particular embodiments, as shown in FIG. 3A, the sealant layer 26 can comprise a piezoelectric material that, in position in the inhaler 50, is electrically coupled to the controller 70 (FIG. 11B). In particular embodiments, as shown in FIG. 14, the layer 26 comprises a piezoelectric film 26*p* that can be configured to extend across all or a portion of the sealant layer 26 proximate the aperture 20*a* in the outer member 20. The layer 26 with the piezoelectric film 26*p* can be configured to flex generally orthogonal to the direction of airflow in response to a predetermined input signal. The input signal may be customized to the particular powder being dispensed. See, e.g., U.S. Patent Application Publication No. US-2004-0025877-A1, the contents of which are hereby incorporated by reference as if recited in full herein. The input signal can be selected based on a programmed library of signals held in memory associated with the controller 70 as noted above.

In certain embodiments, the piezoelectric film material 26*p* comprises a thin film polymer such as PVDF (known as KYNAR® piezo film or polyvinylidene fluoride) or its copolymers such as polyvinylidene fluoride trifluoroethylene (PVDF-TrFe) or TrFe copolymer PVDF tetrafluoroethylene (PVDF-TeFE). In particular embodiments, the piezoelectric polymer material comprises a layer of a thin PVDF film. As used herein, the term "thin film" means that the piezoelectric polymer layer is configured as a structurally flexible or pliable layer that can be sized to be about 10-200 μm thick. In certain embodiments, the piezoelectric polymer film 26*p* can be sized to be less than about 100 μm thick, typically about 20-60 μm thick, and more typically about 28 μm.

The piezoelectric substrate can include a non-piezo active layer, typically comprising aluminum foil, and may, in certain embodiments, include a polymer coating or layer on the top and/or bottom thereof. The non-active layer can be at least about 20 microns thick.

A predetermined conductive material such as metal can be applied to the piezoelectric polymer. The conductive material can be a thin layer of metal or other conductive material that can be inked, stamped, printed (including screen printed), imaged (including, but not limited to, photo-resist imaging), rolled, deposited, sprayed, or otherwise applied to (one or both primary surfaces of) the piezoelectric polymer. Other methods of providing the conductive pattern can also be used, including electron beam evaporation, thermal evaporation, painting, dipping, or sputtering a conductive material or metallic paint and the like or material over the selected surfaces of the piezoelectric substrate (which may comprise a PVDF layer as noted above). In particular embodiments, alternative metallic circuits, foils, surfaces, or techniques can also be employed, such as attaching a conductive Mylar layer or flex circuit over the desired portion of the outer surface of the piezoelectric substrate layer. If flex circuits are used, they may be configured or attached to the piezoelectric substrate layer so as to be substantially transparent to the structure to reduce any potential dampening interference with the substrate layer.

Typically, upper and lower surface metal trace patterns are formed on opposing sides of a piezoelectric polymer material layer but do not connect or contact each other. For example, conductive paint or ink (such as silver or gold) can be applied onto the major surfaces of the package about the elongated channels and associated metal traces such that it does not extend over the perimeter edge portions of the piezoelectric substrate layer, thereby keeping the metal trace patterns on the top and bottom surfaces separated with the piezoelectric substrate layer therebetween. This configuration forms the electrical excitation path when connected to a control system to provide the input/excitation signal for creating the electrical field that activates the deformation of the piezoelectric substrate layer during operation. Typically, one pattern is applied to one side of the piezoelectric substrate and the other side may have a different conductive pattern and/or coverage.

The controller 70 (FIG. 11B) can communicate with a signal generator circuit 81 (signal generating circuitry) that is in communication with the piezoelectric film 26p (or, in other embodiments, other piezoelectrically active material) so that one surface operates with a positive polarity while the other surface has a negative polarity or ground, or vice versa (thereby providing the electric field/voltage differential to excite the piezoelectric substrate). Of course, the polarities can also be rapidly reversed during application of the excitation signal (such as + to −, or + to −) depending on the type of excitation signal used, thereby flexing the piezoelectric material in the region of the receptacle portion. For a more complete discussion of the active excitation path or configuration, see U.S. application Ser. No. 10/204,609, incorporated by reference herein.

In certain embodiments, the drug containment system 10 can include visible indicia and/or can be configured to engage an inhaler to provide audible alerts to warn a user that the container is misaligned in the inhaler 50 and/or that a dose was properly (and/or improperly) inhaled or released from the inhaler device. For example, certain dry powder dose sizes are formulated so that it can be difficult for a user to know whether they have inhaled the medicament (typically the dose is aerosolized and enters the body with little or no taste and/or tactile feel for confirmation). Thus, a sensor can be positioned in communication with the flow path in an inhaler and configured to be in communication with a digital signal processor or microcontroller 70 (FIGS. 11A and 11B), each held in or on the inhaler. In operation, the sensor is configured to detect a selected parameter, such as a difference in weight, a density in the exiting aerosol formulation, and the like, to confirm that the dose was released.

Figure 13:
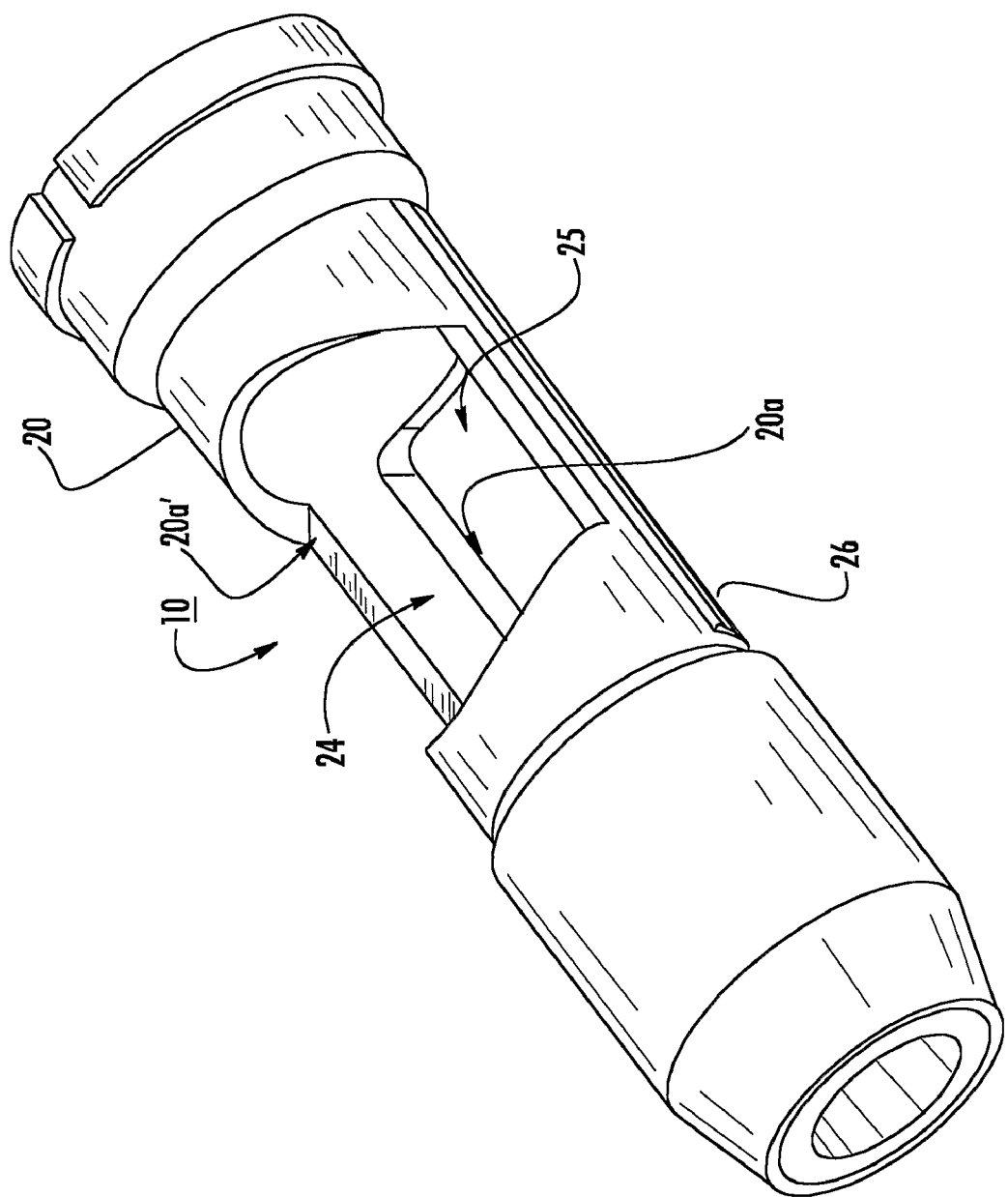
FIG. 13 is an enlarged top perspective view of an outer tubular member shown in FIG. 12A illustrated without the inner member according to embodiments of the present invention.

FIGS. 12-17 illustrate an embodiment of a generally tubular drug containment system 10. Similar to the embodiments discussed above, FIGS. 12A and 12B show that the outer member 20 is configured to slidably snugly receive the inner member 30. As shown, the outer member 20 can include a drug filling port 24 that can be formed by an aperture 20a' in the sidewall of the outer member 25w. Thus, the outer member 20 can include at least two apertures, 20a, 20a', one of which is associated with a drug compartment 25, and the other of which is associated with a filling port 24 as shown in FIG. 13. The drug filling port 24 can have a larger area (axial length and width) than the drug compartment 25. The drug filling port 24 can reside generally above the drug compartment 25. This allows the layer 26 to be attached to the outer member 20, the drug inserted into the drug compartment 25, then the inner member 30 slidably inserted to seal the drug compartment 25 and close the filling aperture 24 to define an enclosed air flow path 40 (open on each opposing end, but not about the sidewalls). In use, the inner member 30 can slide (typically rotated and/or slid forward or rearward and rotated) to open the drug compartment 25 without opening the filling port 24. In other embodiments, the drug compartment 25 can be filled in other ways, not requiring the use of a drug filling port 24 as will be discussed further below.

Figure 14:
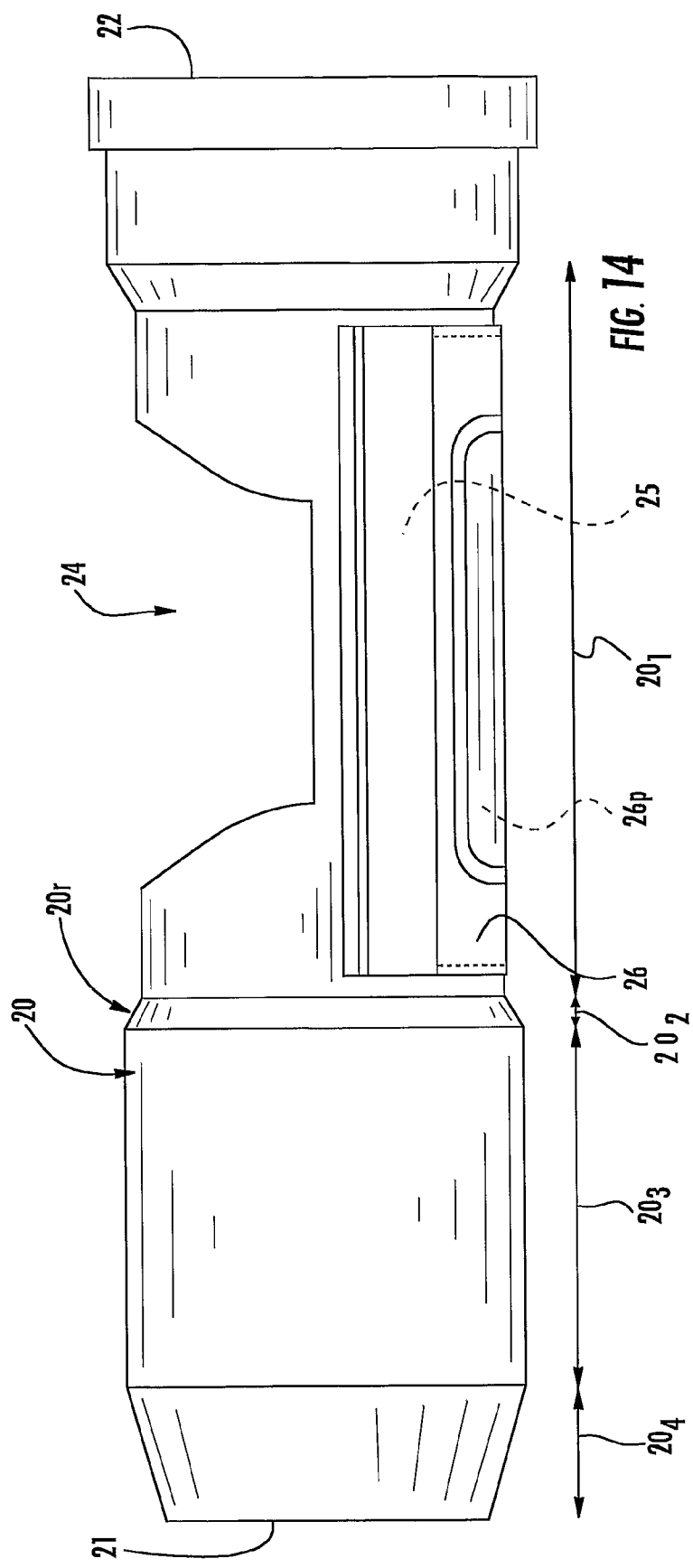
FIG. 14 is an enlarged side view of the device shown in FIG. 13.
Figure 15:
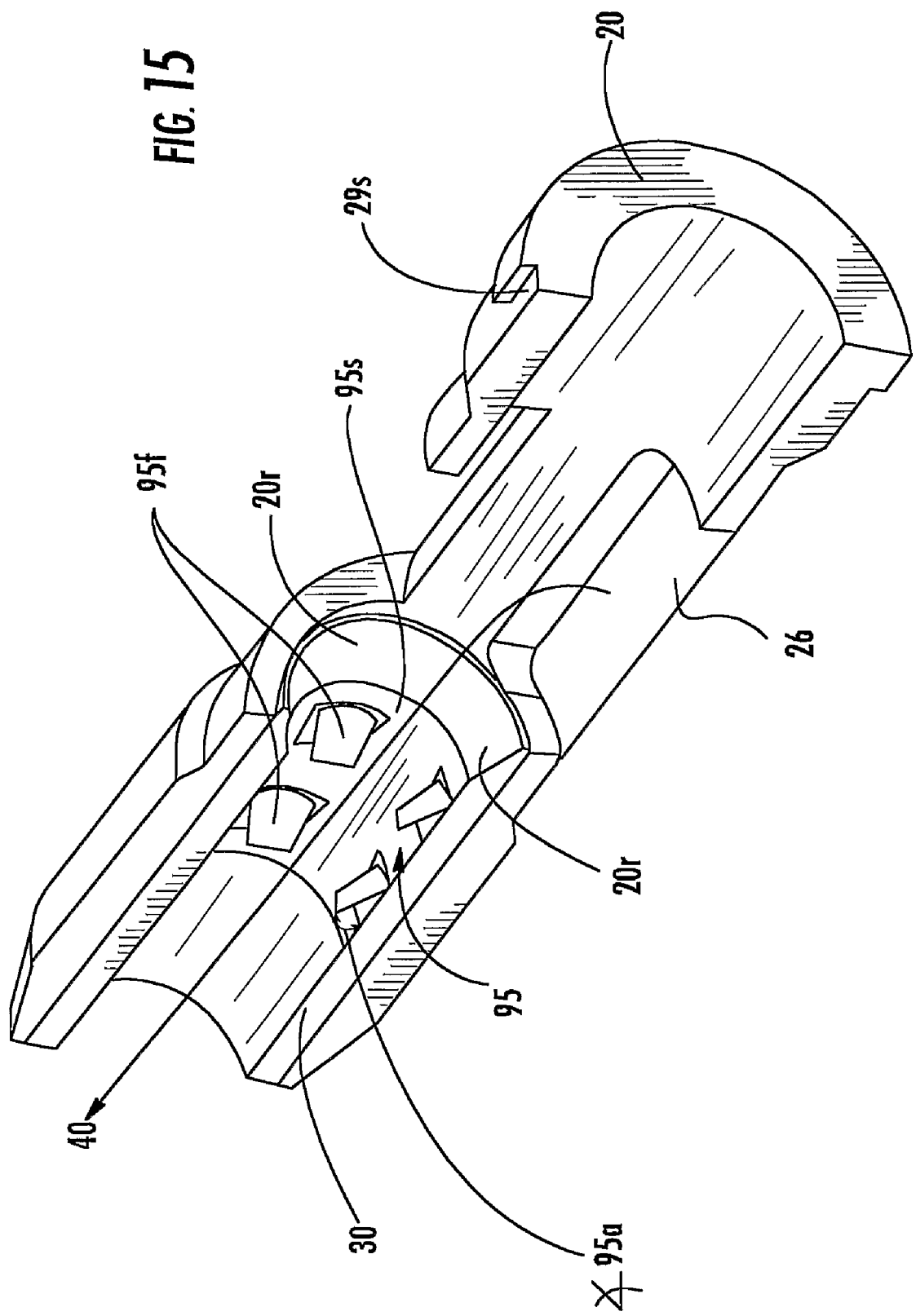
FIG. 15 is an enlarged axial section view of the device shown in FIG. 12A.

FIGS. 14 and 15 illustrate that the outer member 20 can be configured with an inner flow path 40 that includes different cross-sectional widths along its length (i.e., along the flow path 40). As shown, the outer member 20 has a first segment $20_1$ with a first cross-sectional width about the drug compartment 25. This first segment merges into a second segment $20_2$ that tapers into a third segment $20_3$ that merges into a fourth segment $20_4$ that defines a tapered outer forward edge portion. In this embodiment, the third and fourth segments $20_3$, $20_4$ can have a substantially constant inner diameter while the second segment narrows $20_2$ between the first and third segments $20_1$, $20_3$ to create a flow restriction 20r along the flow path 40.

Figure 16:
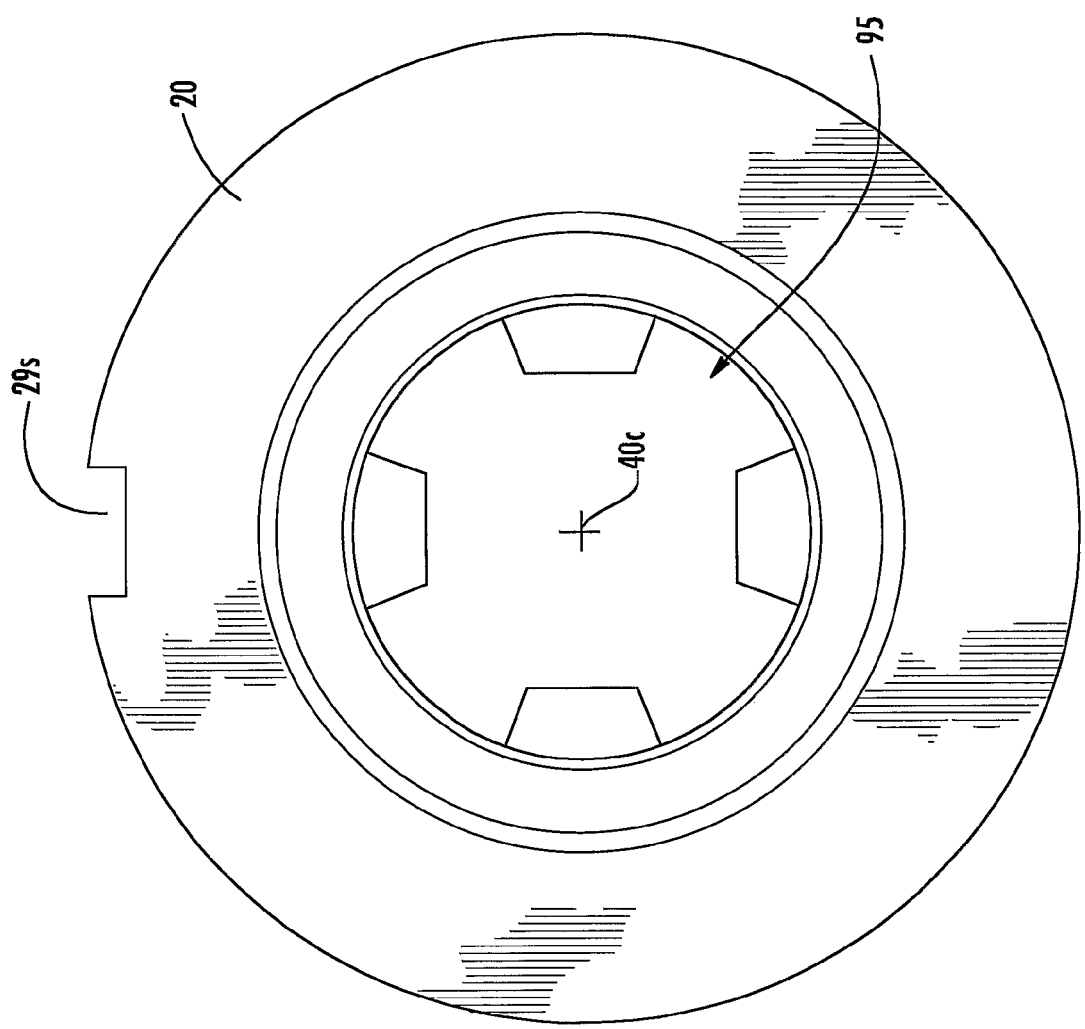
FIG. 16 is an end view of the device shown in FIG. 15.
Figure 17:
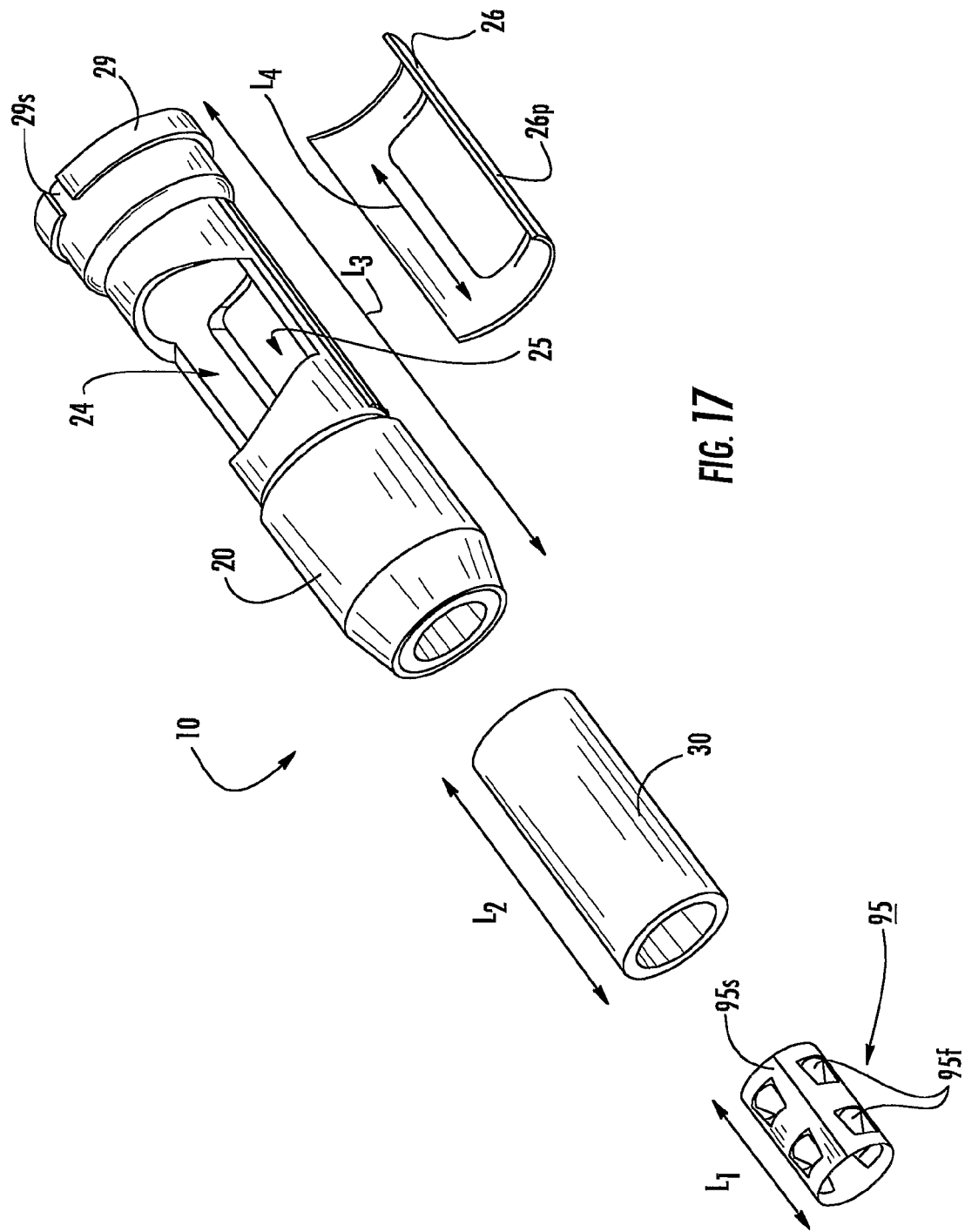
FIG. 17 is an exploded view of the device shown in FIG. 12A.

FIGS. 15-17 also illustrate that a turbulence promoter 95 can be disposed in the flow path 40 downstream of the at least one drug compartment 25. The turbulence promoter 95 can be integrally molded to either the inner or outer member 30, 20. In the embodiment shown, the turbulence promoter 95 is frictionally and/or adhesively attached to the outer member 20 downstream of the inner member 30. However, in other embodiments, the turbulence promoter 95 can be frictionally or adhesively attached to the inner member 30. The turbulence promoter 95 can comprise a polymer material. In other embodiments, the turbulence promoter 95 can comprise a metal such as stainless steel. As shown in FIG. 15, the turbulence promoter 95 can reside in a portion of the third segment $20_3$ of the outer member 20. In other embodiments, the turbulence promoter 95 can be configured to extend inward from the outer member 20 (and may be formed integral thereto) as long as the configuration is positioned to allow the inner member 30 to slide to open the drug compartment(s) 25 (not shown). FIG. 16 illustrates the flow path 40 facing into the paper.

The turbulence promoter 95 can include circumferentially equally spaced apart fingers 95f that taper toward the centerline 40c (FIG. 16) in the flow direction of the flow path 40. As shown, the turbulence promoter 95 can include four fingers 95f spaced at about 90 degrees apart. Lesser or greater numbers of fingers 95f can be used. Other turbulence promoter configurations may also be used. For example, asymmetric variations of the flow path. As shown in FIG. 15, the fingers 95f are generally rigid and can extend from the outer surface of the support 95s at an angle 95a of between about 15-60 degrees.

FIG. 17 illustrates that the turbulence promoter 95 can have a first length $L_1$, the inner member 30 can have a second length $L_2$, the outer member 20 can have a third length $L_3$ and the drug compartment 25 can have a fourth length $L_4$. The outer member length $L_3$ can be the longest, followed by the inner member length $L_2$, then the drug compartment length $L_4$. The turbulence promoter 95 length $L_1$ may be the shortest and can correspond to all or a portion of the length of the third outer member segment $20_3$ (FIG. 14). Typically, the inner member 30 will have a length that extends at least as long as the drug compartment 25 and, where used, the drug filling port 24.

FIGS. 12A-17 also illustrate a collar 29 with a slot 29s on an outer surface of the outer member 20 that is configured to index the outer member 20 in a desired orientation in the inhaler.

Figure 18:
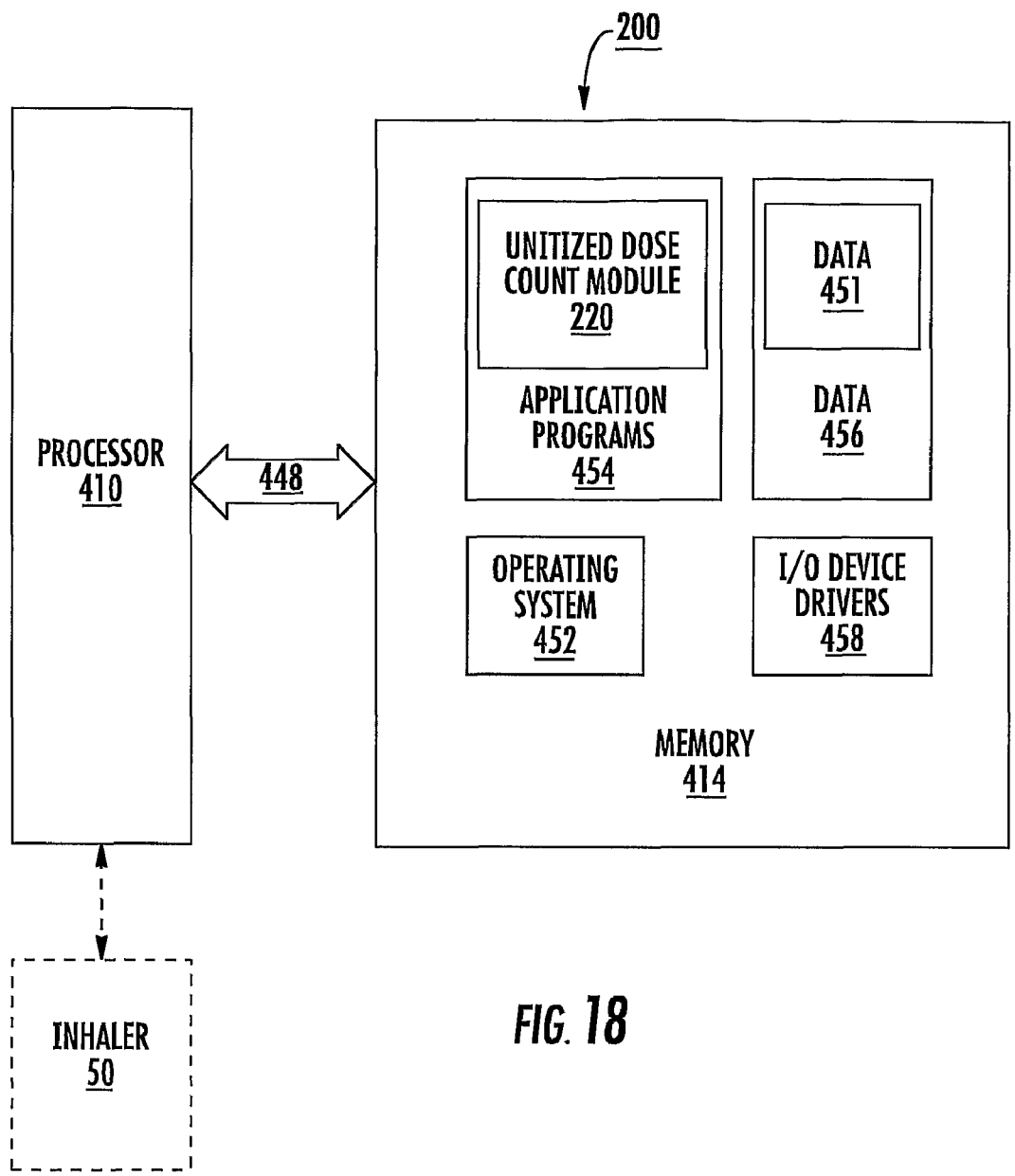
FIG. 18 is a block diagram of a data processing control system according to embodiments of the present invention.

FIG. 18 illustrates an example of a control system 200 that comprises a unitized dose count module 220. The control system 200 may be configured to communicate with a signal generator circuit 81 (FIG. 11B) in the inhaler 10 and communicate with the dry powder containment system 10. The control system can include a processor (such as a digital signal processor) 410 and electronic memory 414. The electronic memory can include, but is not limited to, cache, ROM, PROM, EPROM, EEPROM, flash memory, SRAM, and DRAM.

The system 200 may, in certain embodiments, also include a powder specific non-linear signal generator computer program module that provides the electrical signal characteristics for the drug being dispensed. The signal generator may include a library of a priori signals for different drugs, the appropriate one of which can be selected for operation by the inhaler depending on the drug(s) in the package. The module may be programmed into the memory 410. The system 200 may have a sleep or inactive (or off) mode that is turned to an active mode based on inhaler activation via input from a switch or a sensor. For example, the control system 200 may communicate with a power source 72 (FIGS. 11A, 11B) such as a battery (typically a miniaturized battery, such as a digital camera or pancake type flat battery) to power the signal generator and transmit the electrical signal to the piezoelectric layer or other vibrator means 80 (FIG. 11A). The activation may be carried out automatically based upon input from a sensor and/or activation from an "on" switch.

Examples of an amplitude-modified vibratory signal suitable for vibrating the system 10 holding the dry powder are described in co-pending U.S. patent application Ser. No. 10/434,009, the contents of which are incorporated by reference as if recited in full herein. The vibratory signal can include a kHz carrier frequency (such as about 5 kHz-50 kHz) modified by low modulating frequency (typically about 10-200 Hz). The frequency of the vibration can be modified to match or correspond to the flow characteristics of the dry powder substance held in the package to attempt to reach a resonant frequency(s) to promote uniform drug dispersion into the body. In some embodiments, a non-linear powder-specific dry powder vibratory energy signal comprises a plurality of selected frequencies that can be generated (corresponding to the particular dry powder(s) being currently dispensed) to output the particular signal corresponding to the dry powder(s) then being dispensed. As used herein, the term "non-linear" means that the vibratory action or signal applied to the package to deliver a dose of dry powder to a user has an irregular shape or cycle, typically employing multiple superimposed frequencies, and/or a vibratory frequency line shape that has varying amplitudes (peaks) and peak widths over typical standard intervals (per second, minute, etc.) over time. In contrast to conventional systems, the non-linear vibratory signal input can operate without a fixed single or steady state repeating amplitude at a fixed frequency or cycle. This non-linear vibratory input can be applied to the blister to generate a variable amplitude motion (in either a one, two and/or three-dimensional vibratory motion). The non-linear signal fluidizes the powder in such a way that a powder "flow resonance" is generated allowing active flowable dispensing.

In particular embodiments, the inhaler 50 can include signal-generating circuitry and/or components held thereon or therein which, in operation, are in communication with the system 10 and/or drug compartments 25 to facilitate a complete release of particulate from the drug compartment. The signal generating circuitry may be programmed with a plurality of predetermined different input signals, or if the blister package dispenses only a single dry powder, the signal generator may be programmed with a single signal. Appropriate powder-specific signals, typically used for the channel vibration, can be determined experimentally and/or computationally at an OEM or evaluation site and input into the inhalers (via hardware and/or software components including programmable processors). For additional description of signals and operations to determine same, see co-pending and co-assigned U.S. patent application Ser. Nos. 10/434,009, 10/606,678, 10/607,389, and 10/606,676; the contents of these applications are hereby incorporated by reference in their entireties as if recited in full herein.

In some embodiments, a signal of combined frequencies can be generated to provide a non-linear signal to improve fluidic flow performance. Selected frequencies can be superimposed to generate a single superposition signal (that may also include weighted amplitudes for certain of the selected frequencies or adjustments of relative amplitudes according to the observed frequency distribution). Thus, the vibratory signal can be a derived non-linear oscillatory or vibratory energy signal used to dispense a particular dry powder. In certain embodiments, the output signal used to activate the piezoelectric blister channel may include a plurality of (typically at least three) superpositioned modulating frequencies and a selected carrier frequency. The modulating frequencies can be in the range noted herein (typically between about 10-500 Hz), and, in certain embodiments may include at least three, and typically about four, superpositioned modulating frequencies in the range of between about 10-100 Hz, and more typically, four superpositioned modulating frequencies in the range of between about 10-15 Hz.

While the present invention is illustrated, for example, with reference to the module 220 being an application program in FIG. 18, as will be appreciated by those of skill in the art, other configurations may also be utilized while still benefiting from the teachings of the present invention. Thus, the present invention should not be construed as limited to the configuration of FIG. 18, which is intended to encompass any configuration capable of carrying out the operations described herein.

The I/O data port can be used to transfer information between the data processing system 200 and the inhaler dispensing system controlled by the processor. These components may be conventional components such as those used in many conventional data processing systems which may be configured in accordance with the present invention to operate as described herein.

While the present invention is illustrated, for example, with reference to particular divisions of programs, functions and memories, the present invention should not be construed as limited to such logical divisions. Thus, the present invention should not be construed as limited to the configuration of FIG. 18 but is intended to encompass any configuration capable of carrying out the operations described herein.

Figure 19:
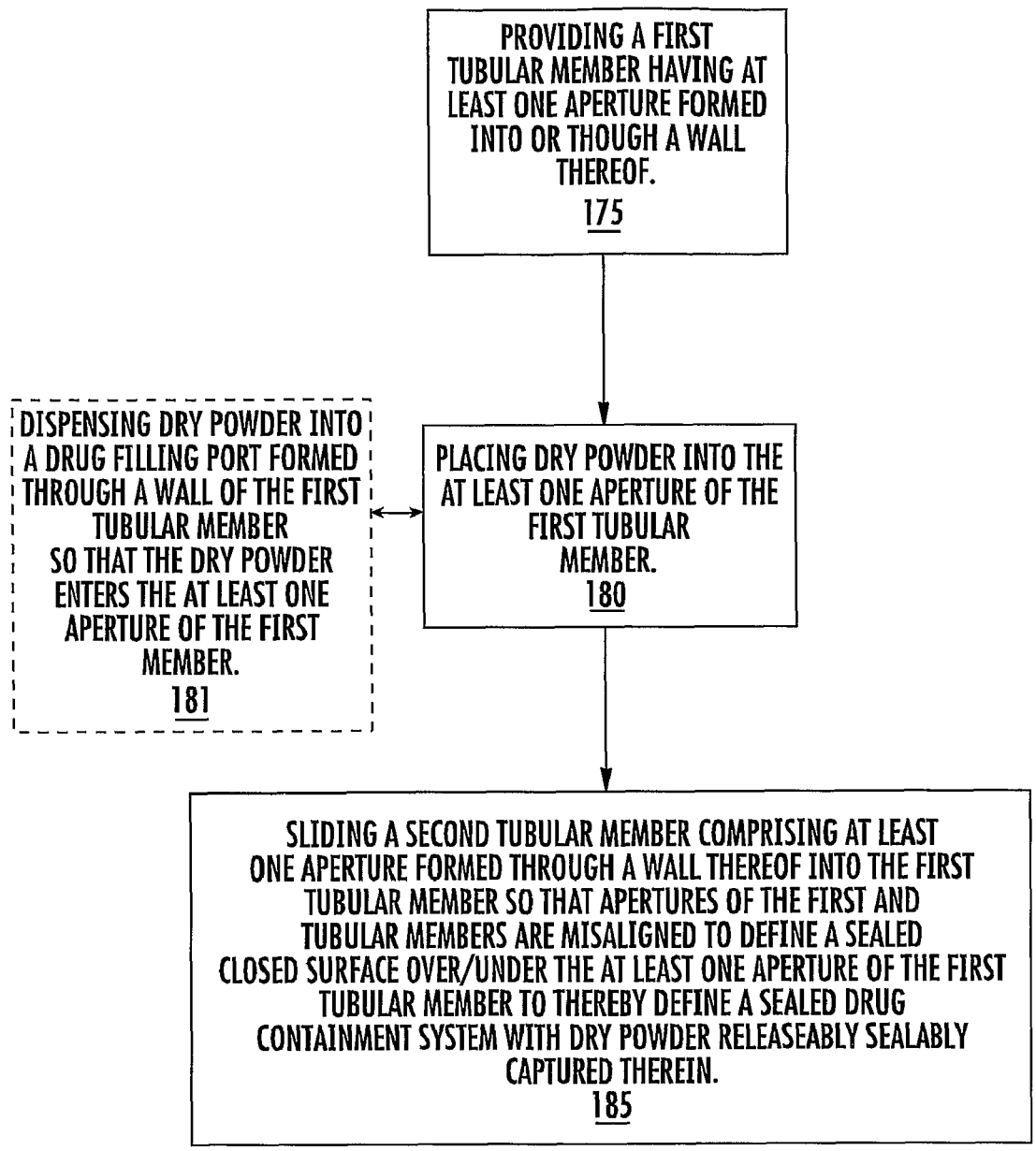
FIG. 19 is a flow chart of operations that can be used to carry out embodiments of the present invention.

FIG. 19 illustrates an example of operations that can be carried out to fabricate a package 10 according to embodiments of the present invention. A first generally tubular member having at least one aperture formed into or through a wall thereof is provided (block 175). A selected dry powder drug and/or medicament is placed into the at least one aperture of the first generally tubular member (block 180). Optionally, the dry powder can be dispensed into the at least one aperture through a drug filling port also disposed in the first generally tubular member (block 181). A second generally tubular member comprising at least one aperture formed through a wall thereof is slid into the first generally tubular so that the apertures of the first and second generally tubular members are misaligned to define a closed surface over/under the at least one aperture of the first generally tubular member to thereby define a sealed drug containment system with dry powder releasably sealably captured therein (block 185).

The inner and outer members can be elastomeric generally rigid bodies. The drug compartment wells can be filled with a predetermined meted (typically bolus amount when either dispensed alone or with another meted dry powder medicament) amount of dry powder. The term "filled" includes providing an amount that is less than the volumetric capacity of the well. The members may be sterilized prior to (after the wells are formed) depositing the dry powder therein. Sealant material can be applied to form the floor or ceiling of each drug compartment.

The inner member can be slid into the outer member and the drug filled by depositing the dry powder directly through the outermost surface of the outer tubular member. The sealant layer 26 can then be attached to seal the drug compartment. Alternatively, the sealant material can be applied before filling and the drug filling port used to fill the drug compartment(s). Similarly, the outer member can have a closed outer surface (without a through aperture) not requiring the use of an outer sealant layer, and the drug filling port can be used to fill the drug compartment, then the inner member inserted to seal the drug containment system.

Certain filling and/or inhaler use operations may be automated and/or carried out using computer programs and automated equipment.

The flowcharts and block diagrams of certain of the figures herein illustrate the architecture, functionality, and operation of possible implementations of dry powder-specific dispensing and/or vibratory energy excitation means according to the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order, depending upon the functionality involved.

In certain embodiments, the powder specific vibration energy signals are non-linear and the inhaler can include computer program code that automatically selectively adjusts the output of the vibration energy signal based on the identified dry powder being dispensed. The vibration energy output signals for the dry powders being dispensed can be based on data obtained from a fractal mass flow analysis or other suitable analysis of the dry powder being administered to the user. The inhaler may be particularly suited to dispense low-density dry powder.

Certain embodiments may be particularly suitable for dispensing medication to diabetic patients, cystic fibrosis patients and/or patients having diseases or impairments where variable bolus medicaments are desired. Other embodiments may be particularly suitable for dispensing narcotics, hormones and/or infertility treatments.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. An inhaler, comprising:
a body having an inspiratory airflow path and an elongate chamber configured to receive a generally tubular unitized drug containment system;
a generally tubular unitized drug containment system residing in the elongate chamber, the generally tubular unitized drug containment system having a generally open downstream end portion and at least one sealed drug compartment holding dry powder residing upstream of the downstream end portion, wherein the generally tubular drug containment system comprises cooperating, abutting inner and outer generally tubular members that slide to open the sealed drug compartment to thereby release dry powder from the drug compartment without piercing for inhalation;
a display and a user input operatively associated with the display held by the body; and
an electronic counter held by the body in communication with the display, the counter configured to decrement a dose amount needed after a sub-bolus dose is delivered so that a user can readily ascertain which additional unitized drug containment system to select.

2. An inhaler according to claim 1, wherein the generally tubular container comprises electronically readable dose indicia.

3. An inhaler according to claim 1, wherein the inner and outer generally tubular members define a drug flow channel, and wherein each of the inner and outer tubular members comprise a generally open downstream end portion.

4. An inhaler according to claim 1, wherein the inhaler chamber comprises an entry port that is configured to slidably receive the generally tubular drug containment system therein.

5. An inhaler according to claim 1, wherein the user input comprises positive and negative user inputs to allow a user to enter an increase and/or a decrease of a dose amount desired.

6. An inhaler according to claim 1, further comprising a vibrator operatively associated with the elongate chamber configured to vibrate dry powder in the inspiratory airflow path during operation.

7. An inhaler according to claim 1, further comprising an electronic reader in communication with the display and counter, the electronic reader configured to automatically read a dose amount associated with the unitized generally tubular drug containment system in the chamber so that the inhaler can automatically decrement a bolus amount remaining.

8. An inhaler according to claim 1, wherein inhaler is configured to releaseably hold a plurality of user selectable generally tubular drug containment systems for storage.

9. An inhaler according to claim 1, wherein the chamber is configured to receive the generally tubular drug containment system in a selected orientation to locate a drug compartment in the generally tubular drug containment system in target top or bottom location in the chamber.

10. An inhaler according to claim 9, wherein the chamber comprises a projection, and an outer surface of the tubular drug containment system comprises an axially extending slot that matably engages the projection to maintain the desired orientation of the tubular drug containment system in the chamber.

11. An inhaler according to claim 9, wherein the chamber is configured to matably engage the drug containment system so that the drug compartment is proximate a bottom portion of the air flow path with the inner member window aligned thereabove.

12. An inhaler according to claim 9, wherein the chamber is configured to matably engage the drug containment system so that the drug compartment is proximate a top portion of the air flow path with the inner member window aligned therebelow.

* * * * *